United States Patent
Paten et al.

(10) Patent No.: US 11,179,494 B2
(45) Date of Patent: Nov. 23, 2021

(54) COLLAGENOUS TISSUE REPAIR DEVICE

(71) Applicant: Northeastern University, Boston, MA (US)

(72) Inventors: Jeffrey A. Paten, Hyde Park, MA (US); Jeffrey W. Ruberti, Lexington, MA (US)

(73) Assignee: Northeastern University, Boston, MA (US)

( * ) Notice: Subject to any disclaimer, the term of this patent is extended or adjusted under 35 U.S.C. 154(b) by 1107 days.

(21) Appl. No.: 15/536,358

(22) PCT Filed: Dec. 15, 2015

(86) PCT No.: PCT/US2015/065919
§ 371 (c)(1),
(2) Date: Nov. 13, 2017

(87) PCT Pub. No.: WO2016/100411
PCT Pub. Date: Jun. 23, 2016

(65) Prior Publication Data
US 2017/0360986 A1    Dec. 21, 2017

Related U.S. Application Data

(60) Provisional application No. 62/232,793, filed on Sep. 25, 2015, provisional application No. 62/092,162, filed on Dec. 15, 2014.

(51) Int. Cl.
*A61L 27/24* (2006.01)
*A61M 5/142* (2006.01)
(Continued)

(52) U.S. Cl.
CPC .............. *A61L 27/24* (2013.01); *A61H 1/008* (2013.01); *A61H 1/02* (2013.01); *A61K 9/0019* (2013.01);
(Continued)

(58) Field of Classification Search
CPC .......... A61H 1/008; A61H 1/02; A61L 27/24; A61L 27/50; A61L 27/54; A61L 2300/41;
(Continued)

(56) References Cited

U.S. PATENT DOCUMENTS 5,077,313 A    12/1991  Lubec
5,316,914 A *  5/1994  Oshima .............. G01N 33/6887
                                             435/7.94
(Continued)

FOREIGN PATENT DOCUMENTS

EP       1342481 A1    9/2003
WO    2005/058385 A2    6/2005
(Continued)

OTHER PUBLICATIONS

Shang S-W et al. Molecular mechanism of force induced stabilization of collagen against enzymatic breakdown Biomaterials. May 2012 ; 33(15):3852-3859.
(Continued)

*Primary Examiner* — Valerie L Woodward
(74) *Attorney, Agent, or Firm* — Verrill Dana, LLP

(57) ABSTRACT

Methods and devices for tissue remodeling and repair of collagenous tissues, including tendons, ligaments, and bone, as well as scalable connective tissue manufacturing, are provided. Collagen fibers are assembled by extensional strain-induced flow crystallization of collagen monomers. Extensional strain also drives the fusion of already formed short collagen fibrils to produce long-range, continuous fibers. Wearable devices for controlled tissue remodeling and wound healing deliver a tissue remodeling solution to a tissue repair site. The remodeling solution, together with appropriate application of strain to the tissue remodeling site, accelerate healing, prevent injury, and reduce scar formation.

34 Claims, 16 Drawing Sheets

(51) Int. Cl.
| | |
|---|---|
| A61K 38/39 | (2006.01) |
| A61K 47/18 | (2017.01) |
| A61K 9/00 | (2006.01) |
| A61K 38/48 | (2006.01) |
| A61K 38/47 | (2006.01) |
| A61H 1/00 | (2006.01) |
| A61H 1/02 | (2006.01) |
| A61L 27/50 | (2006.01) |
| A61L 27/54 | (2006.01) |
| D01D 5/00 | (2006.01) |
| D01F 4/00 | (2006.01) |
| A61M 5/14 | (2006.01) |
| A61N 1/04 | (2006.01) |

(52) U.S. Cl.
CPC ............. *A61K 38/39* (2013.01); *A61K 38/47* (2013.01); *A61K 38/4873* (2013.01); *A61K 38/4886* (2013.01); *A61K 47/183* (2013.01); *A61L 27/50* (2013.01); *A61L 27/54* (2013.01); *A61M 5/142* (2013.01); *C12Y 302/01035* (2013.01); *C12Y 304/22001* (2013.01); *C12Y 304/24* (2013.01); *C12Y 304/24007* (2013.01); *D01D 5/00* (2013.01); *D01F 4/00* (2013.01); *A61L 2300/41* (2013.01); *A61L 2300/426* (2013.01); *A61L 2400/06* (2013.01); *A61L 2430/10* (2013.01); *A61M 5/14* (2013.01); *A61M 5/14248* (2013.01); *A61M 2202/095* (2013.01); *A61M 2205/50* (2013.01); *A61N 1/0456* (2013.01); *D10B 2509/00* (2013.01)

(58) Field of Classification Search
CPC ........... A61L 2300/426; A61L 2430/10; A61L 2400/06; D01D 5/00; D01F 4/00; A61M 5/14248; A61M 2205/50; A61M 2202/095; A61M 2005/1726; A61N 1/0456; D10B 2509/00; A61K 9/0019; A61K 9/0021; A61K 38/39
See application file for complete search history.

(56) References Cited

U.S. PATENT DOCUMENTS

| | | | | |
|---|---|---|---|---|
| 5,433,735 | A * | 7/1995 | Zanakis | A61N 1/205 607/116 |
| 5,863,715 | A * | 1/1999 | Rajotte | A01N 1/02 165/263 |
| 6,592,794 | B1 * | 7/2003 | Bachrach | D01F 4/00 264/178 F |
| 8,338,570 | B2 | 12/2012 | Saeidi et al. | |
| 8,840,665 | B2 | 9/2014 | Young et al. | |
| 2001/0004710 | A1 * | 6/2001 | Felt | C08L 75/04 623/17.12 |
| 2001/0051778 | A1 | 12/2001 | Sevier et al. | |
| 2002/0038150 | A1 * | 3/2002 | Urry | C08F 293/00 623/23.72 |
| 2002/0049483 | A1 | 4/2002 | Knowlton | |
| 2002/0090725 | A1 | 7/2002 | Simpson et al. | |
| 2002/0123750 | A1 * | 9/2002 | Eisermann | A61F 2/441 606/285 |
| 2005/0267400 | A1 * | 12/2005 | Haarala | A61M 1/3653 604/43 |
| 2006/0134779 | A1 * | 6/2006 | Banes | C12N 5/066 435/325 |
| 2006/0251702 | A1 | 11/2006 | Janis et al. | |
| 2008/0097426 | A1 * | 4/2008 | Root | A61B 18/24 606/41 |
| 2009/0171467 | A1 | 7/2009 | Mann et al. | |
| 2010/0048473 | A1 | 2/2010 | Chaikof et al. | |
| 2010/0227043 | A1 * | 9/2010 | Fuller | C08J 5/00 427/2.24 |
| 2011/0166325 | A1 * | 7/2011 | Saeidi | C08H 1/06 530/356 |
| 2013/0013065 | A1 | 1/2013 | Bills | |
| 2013/0144144 | A1 * | 6/2013 | Laster | A61B 5/14532 600/365 |
| 2013/0295081 | A1 | 11/2013 | Guelcher et al. | |
| 2014/0039451 | A1 * | 2/2014 | Bangera | G05B 19/4099 604/506 |
| 2014/0316323 | A1 * | 10/2014 | Kanevsky | A61F 13/0243 602/53 |
| 2014/0342394 | A1 * | 11/2014 | Parker | G01N 33/5088 435/30 |
| 2014/0353873 | A1 | 12/2014 | Ruberti et al. | |

FOREIGN PATENT DOCUMENTS

| | | |
|---|---|---|
| WO | 2014121303 A1 | 8/2014 |
| WO | 2014144215 A1 | 9/2014 |

OTHER PUBLICATIONS

Flynn B et al. Mechanical Strain Stabilizes Reconstituted Collagen Fibrils against Enzymatic Degradation by Mammalian Collagenase Matrix Metalloproteinase 8 (MMP-8). PLoS ONE. vol. 5, Issue 8, e12337 (2010).

Fujisato T et al. Effect of basic fibroblast growth factor on cartilage regeneration in chondrocyte-seeded collagen sponge scaffold. vol. 17, Issue 2, pp. 155-162 (1996).

Kozel, B. A., Ciliberto, C. H. & Mecham, R. P. Deposition of tropoelastin into the extracellular matrix requires a competent elastic fiber scaffold but not live cells Matrix Biol 23, 23-34 (2004).

Seifert, C. & Grater, F. Protein mechanics: how force regulates molecular function. Biochim Biophys Acta 1830, 4762-4768 (2013).

Paten J. Investigation into the Mechano-Chemistry of De Novo Collagen Assembly. Dissertation. Northeastern University (2014).

\* cited by examiner

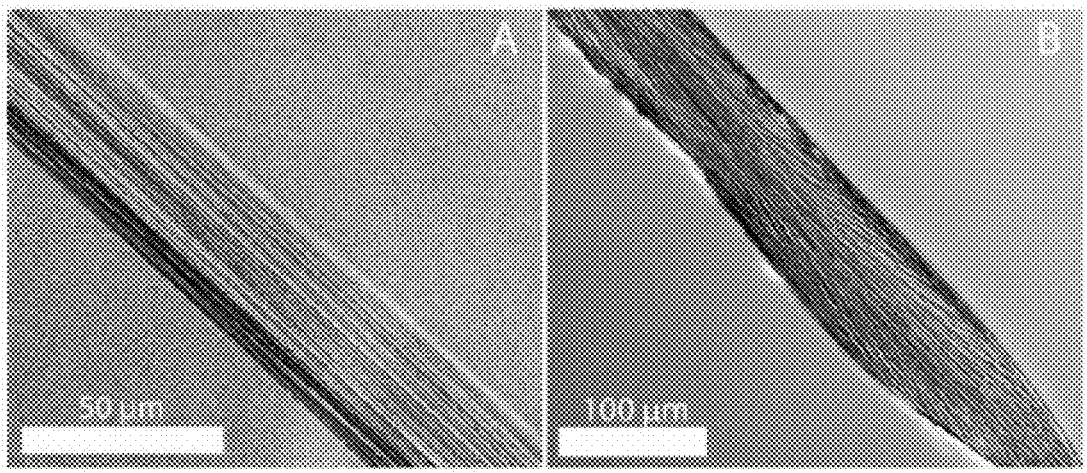
FIG. 6A   FIG. 6B
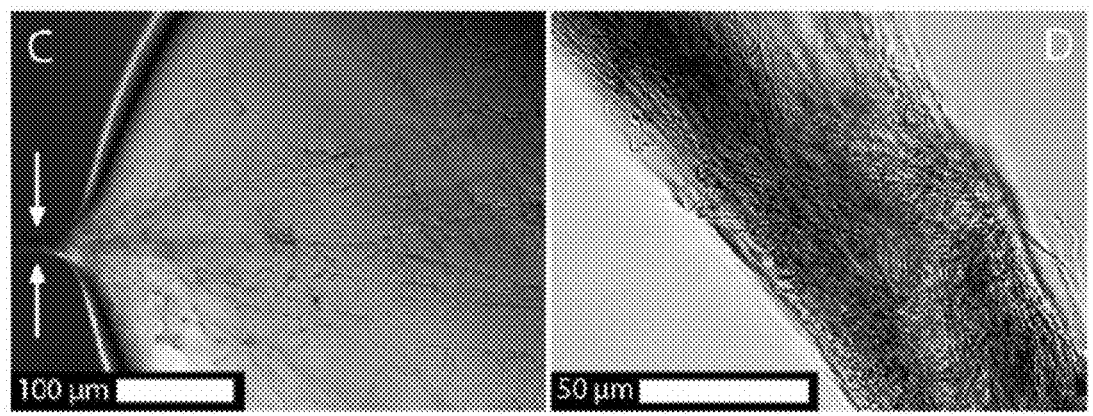
FIG. 6C   FIG. 6D
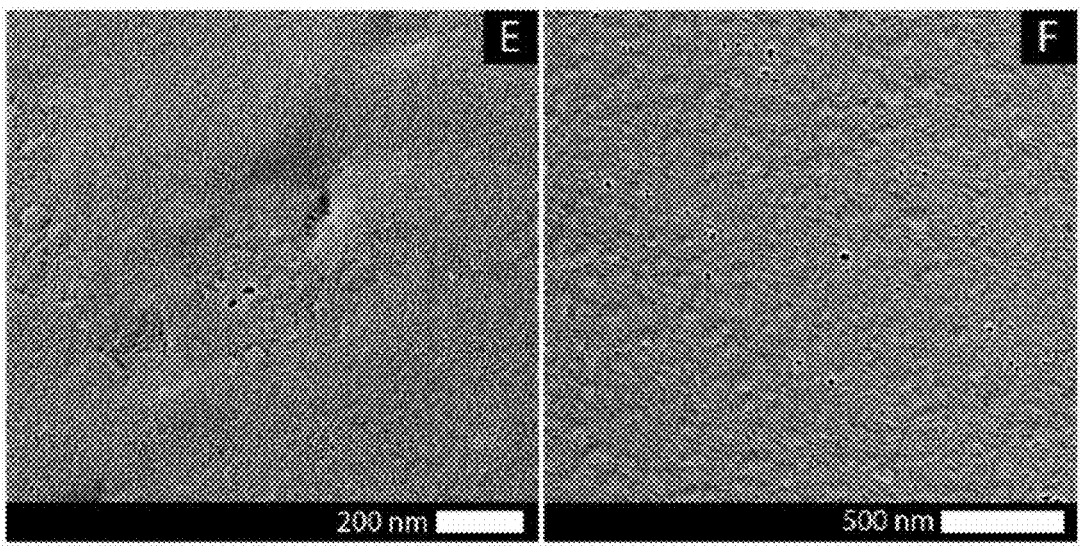
FIG. 6E   FIG. 6F

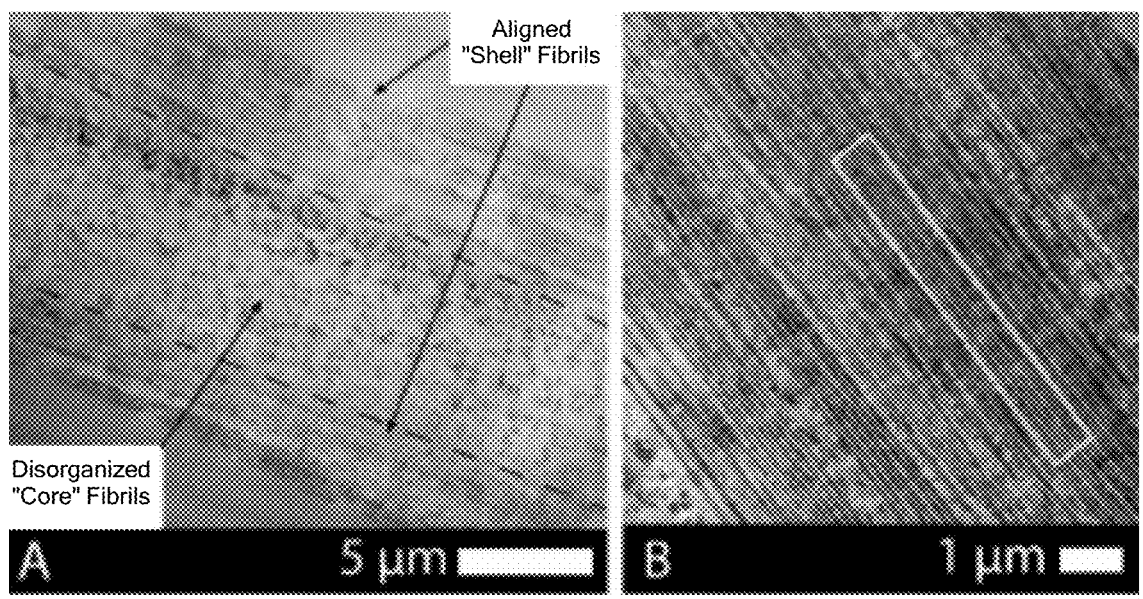
FIG. 8A   FIG. 8B
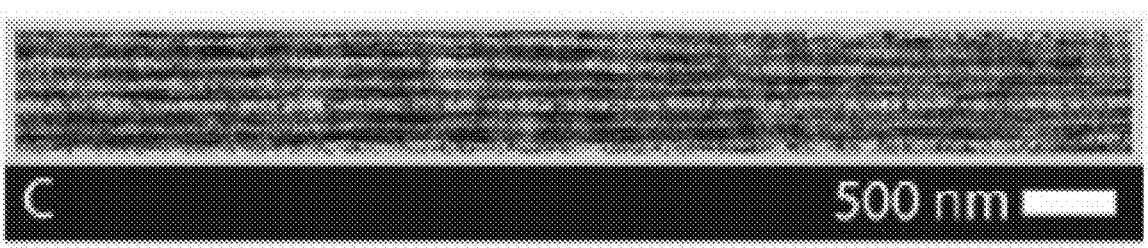
FIG. 8C
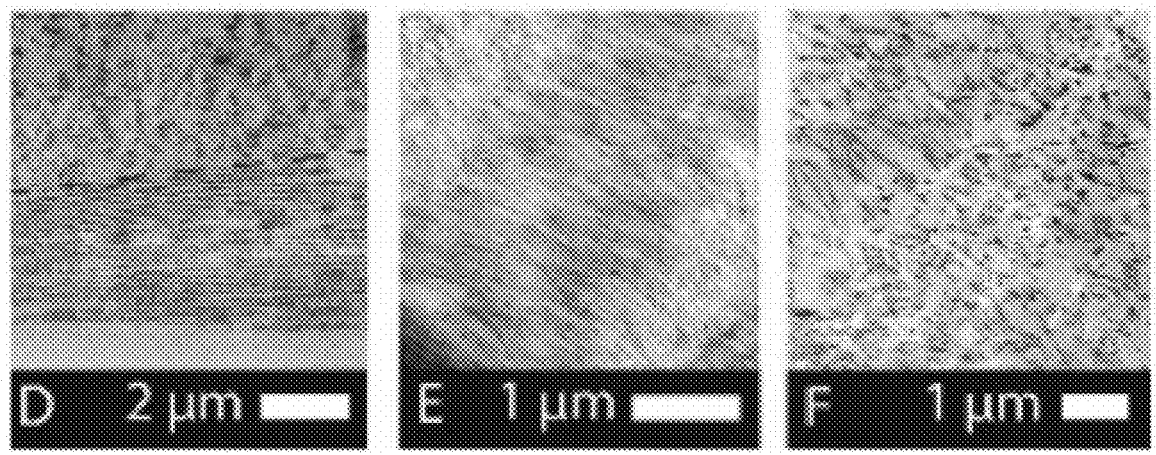
FIG. 8D   FIG. 8E   FIG. 8F

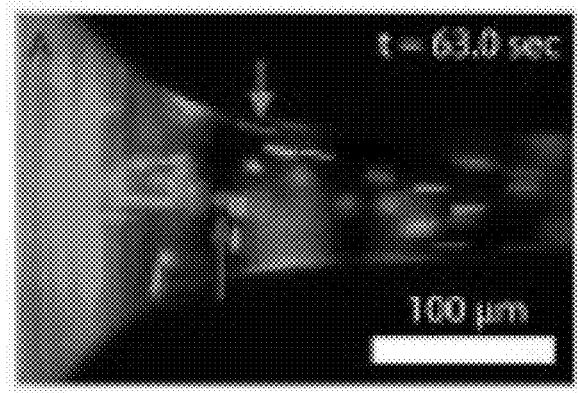
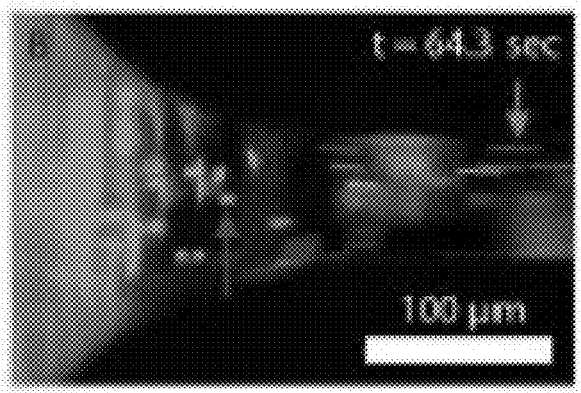
FIG. 9A  FIG. 9B
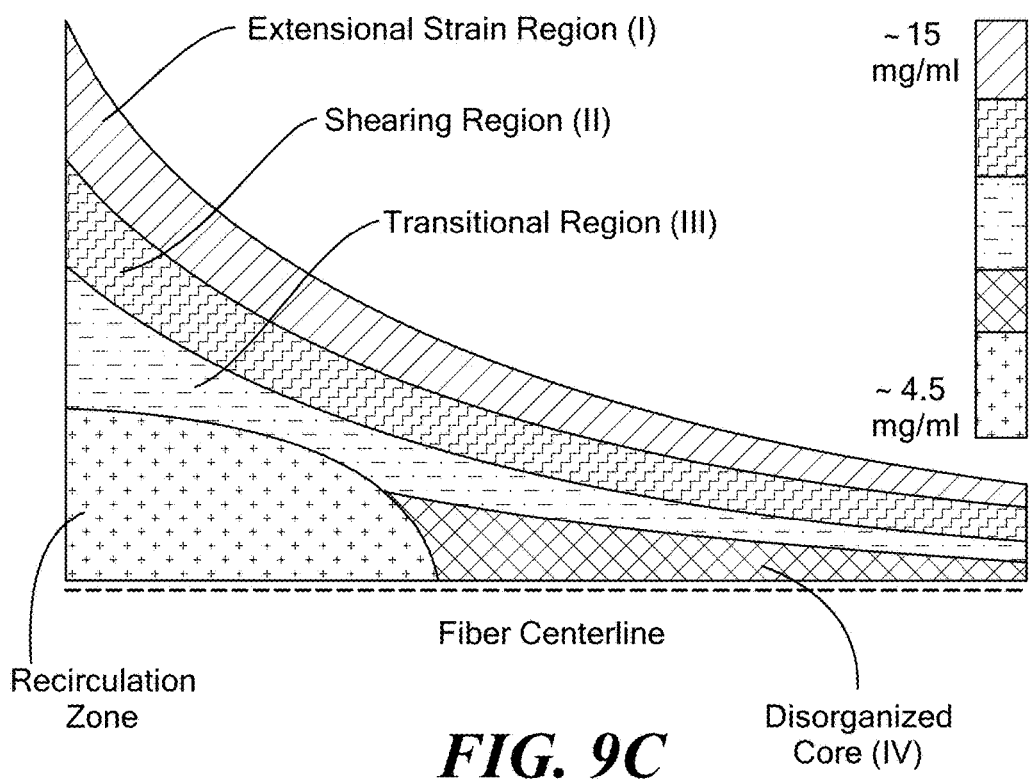
FIG. 9C

COLLAGENOUS TISSUE REPAIR DEVICE

STATEMENT REGARDING FEDERALLY SPONSORED RESEARCH OR DEVELOPMENT

The invention was made with government support under Grant Number EY015500 awarded by the National Institutes of Health. The government has certain rights in the invention.

BACKGROUND

Extracellular matrix (ECM) tissues naturally heal slowly due to low cell populations, low vascularity, and age-related lowered metabolic activity. The primary biological response to ECM injury is the formation of scar tissue, which has reduced molecular organization, diminished mechanical properties, and often results in inferior mobility. When the injury separates the tissue by a distance too great to be bridged by scar tissue, surgical techniques are implemented which utilize sutures to hold the ruptured pieces of tissue in close proximity. However, the actual repair is still entirely reliant on molecular production by the cells. Further, in many ECM injuries, the cells vacate the injury area or undergo apoptosis, further imparing the ability of the tissue to mount a repair. The rate-limiting step in the healing process is the amount of time it takes for cells to secrete the ECM molecules required to facilitate repair. Furthermore, the altered mechanical state and inflammatory response by the immune system miscue which proteins are secreted and their corresponding concentrations.

SUMMARY OF THE INVENTION

The invention relates to the repair of damaged biological tissues, particularly collagenous tissue such as the extracellular matrix (ECM). Devices, systems, and methods are provided that accelerate the rate at which the repair occurs and improve the extent and quality of the restoration of damaged tissues.

The approach described herein regulates the molecular environment of a tissue undergoing repair or remodeling by delivering an exogenous mixture of biomolecules and/or their precursors to alleviate the burden and reliance placed on the endogenous biological response. The components of the mixture are similar to those present during wound healing and/or tissue development. Additional components, such as anti-inflammatory molecules or immune suppressing molecules, can also be included. The mixture of molecules contributes to and accelerates the repair process.

One aspect of the invention is a method of promoting collagenous tissue remodeling in a subject in need thereof. The method includes the steps of: (a) administering to a tissue remodeling site in the subject a tissue remodeling solution; and (b) inducing strain or strain rate at the tissue remodeling site, whereby collagen incorporation, collagen fibril assembly, or collagen fibril disassembly is stimulated at the tissue remodeling site. In some embodiments, the method includes the step (a0), prior to step (a), of implanting an internal sheath into the subject, wherein the sheath surrounds the tissue remodeling site. In some embodiments, the method further includes: (c) monitoring one or more parameters in a sample of extracellular fluid obtained from the tissue remodeling site; and (d) adjusting the administration or composition of the remodeling solution based on said one or more parameters.

Another aspect of the invention is a device for promoting tissue remodeling in a subject in need thereof. The device includes: (i) a dispensing module, comprising a reservoir for a tissue remodeling solution and an infusion pump for transporting the tissue remodeling solution from the reservoir; (ii) a delivery catheter for transporting the tissue remodeling solution from the infusion pump to a tissue remodeling site in the body of the subject; and (iii) a programmable control module for controlling the pump and optionally the composition of the tissue remodeling solution, wherein the control module is programmed to control tissue remodeling by regulating delivery and/or composition of the tissue remodeling solution to the tissue remodeling site, so as to promote collagen fibril assembly, disassembly, and/or realignment at the tissue remodeling site. In some embodiments, the dispensing module further includes one or more additional reservoirs for one or more additional reagent solutions and a mixing system for mixing the one or more additional reagent solutions with the tissue remodeling solution prior to its transport to the tissue remodeling site. In some embodiments, the device further includes (iv) a return catheter for transporting extracellular fluid from the tissue remodeling site back to the device for analysis. In some embodiments, the dispensing module further includes a mixing system for mixing the returned extracellular fluid with the tissue remodeling solution and/or with one or more additional reagents for transport to the tissue remodeling site through the delivery catheter. Optionally, the dispensing module further includes a microdialysis module for conditioning of returned extracellular fluid before it is transported back to the tissue remodeling site. Some embodiments of the device further include (v) a sensor for detecting a concentration of one or more components of extracellular matrix fluid at the tissue remodeling site, the sensor providing an output related to the one or more components to the control module. Some embodiments of the device include a muscle stimulation module that provides electrical stimulation of one or more muscles of the subject in the area surrounding the tissue remodeling site. Some embodiments of the device include a passive motion device that induces extensional strain at the tissue remodeling site.

Yet another aspect of the invention is a kit that include the device described above, a tissue remodeling solution, and optionally one or more reagent solutions for use with the device.

Still another aspect of the invention is a kit including the device described above and one or more sheaths for use with the device.

Another aspect of the invention is an in vitro method of producing one or more collagen fibrils. The method includes the steps of: (a) providing a collagen solution initially devoid of collagen fibrils; and (b) applying mechanical stress to the solution, whereby collagen from the solution assembles into one or more collagen fibrils.

Yet another aspect of the invention is a method for producing an artificial tissue scaffold. The method includes the step of performing the in vitro method of producing one or more collagen fibrils described above while the collagen monomer solution is in a mold, wherein the shape of the mold provides the shape of the tissue scaffold.

Still another aspect of the invention is a method to aid in preventing injury or tissue damage in a subject in need thereof. The method includes the steps of: (a) administering to a tissue remodeling site in the subject a tissue remodeling solution, wherein the tissue remodeling site is suspected of being subject to future injury or tissue damage; and (b) inducing strain or strain rate to the tissue remodeling site, whereby collagen fibril assembly or disassembly is stimulated at the tissue remodeling site.

Another aspect of the invention is a tissue remodeling solution that contains monomeric collagen, oligomeric collagen, and one or more components selected from the group consisting of: extracellular matrix enzymes, cross-linking agents, immunosuppressive agents, pH modifying agents, ionic strength modifying agents, osmicants, plasticizers, fibroblasts, mesenchymal stem cells, cell migration promoters, collagen fibril fragments, proteoglycans, glycosaminoglycans, hyaluronic acid, glycoproteins, fibronectin, elastin, fibrinogen, thrombin, thrombospondin, silk, and growth factors. The tissue remodeling solution also can contain one or more factors that delay collagen assembly or increase a collagen solubility limit, such as glucose, heat shock proteins, L-arginine, L-glutamine, polyarginine, polyglutamine, and anionic polymers; a cross-linking agent such as transglutaminase and lysyl oxidase; extracellular matrix enzymes such as matrix metalloproteinases (MMPs), cathepsins, and bacterial collagenases; and immunosuppressive agents, such as anti-inflammatory agents.

The invention can be further summarized by the following list of items

1. A method of promoting collagenous tissue remodeling in a subject in need thereof, the method comprising the steps of:
    (a) administering to a tissue remodeling site in the subject a tissue remodeling solution; and
    (b) inducing strain or strain rate at the tissue remodeling site, whereby collagen incorporation, collagen fibril assembly, collagen fibril fusion, and/or collagen fibril disassembly is stimulated at the tissue remodeling site.
2. The method of item 1, wherein the tissue remodeling solution comprises a mixture of collagen monomers and/or oligomers and is devoid of pre-existing collagen fibrils.
3. The method of item 1 or item 2, wherein the tissue remodeling solution comprises collagen monomers, dimers, trimers, aggregates, and/or fibrils.
4. The method of any of the preceding items, wherein the tissue remodeling solution further comprises one or more components selected from the group consisting of extracellular matrix enzymes, cross-linking agents, immunosuppressive agents, pH modifying agents, ionic strength modifying agents, osmicants, plasticizers, fibroblasts, mesenchymal stem cells, cell migration promoters, collagen fibril fragments, proteoglycans, glycosaminoglycans, hyaluronic acid, glycoproteins, fibronectin, elastin, fibrinogen, thrombin, thrombospondin, silk, and growth factors.
5. The method of item 4, wherein the tissue remodeling solution further comprises one or more factors that delay collagen assembly or increase a collagen solubility limit.
6. The method of item 5, wherein the one or more factors that delay collagen assembly are selected from the group consisting of glucose, heat shock proteins, L-arginine, L-glutamine, polyarginine, polyglutamine, and anionic polymers.
7. The method of item 6, wherein the tissue remodeling solution comprises a cross-linking agent selected from transglutaminase, lysyl oxidase, glutaraldehyde, paraformaldehyde, and riboflavin.
8. The method of item 4, wherein the tissue remodeling solution comprises an extracellular matrix enzyme selected from matrix metalloproteinases (MMPs), cathepsins, bacterial collagenases, and gagases, such as chondroitinase or hyaluronidase.
9. The method of item 4, wherein the tissue remodeling solution comprises an immunosuppressive agent, and the immunosuppressive agent is an anti-inflammatory agent.
10. The method of any of the preceding items, wherein the tissue remodeling solution is administered by one or more injections or by continuous or intermittent infusion.
11. The method of any of the preceding items, wherein strain rate is induced cyclically or intermittently, and provides either extension or compression at the tissue remodeling site.
12. The method of item 11, wherein the strain rate at the remodeling site is from about 0.001 $sec^{-1}$ to about 10 $sec^{-1}$.
13. The method of item 11, wherein collagen fibril assembly is stimulated by flow-induced crystallization.
14. The method of any of the preceding items, wherein static strain is induced and held, either cyclically or intermittently.
15. The method of item 14, wherein the static strain at the remodeling site is from 0 to about 2, and collagen fibril assembly is stimulated by incorporation of collagen monomers and/or oligomers into pre-existing collagen fibrils.
16. The method of item 14, wherein the induced static strain at the remodeling site is from 0 to about 2, and collagen fibril dissociation or degradation is stimulated by one or more of temperature or enzymes selected from matrix metalloproteinases (MMPs), cathepsins, and bacterial collagenases.
17. The method of any of the preceding items, wherein extensional or compressive strain, or an extensional strain rate, is induced at the remodeling site by physical therapy, massage, stretching, an exercise program, electrical muscle stimulation, or a continuous passive motion device.
18. The method of any of the preceding items, wherein administering the tissue remodeling solution is performed according to a program that determines the composition or amount of the tissue remodeling solution to be administered and the timing of administering the tissue remodeling solution.
19. The method of item 18, wherein the program determines the presence or absence and concentration (if present) of one or more components of the tissue remodeling solution selected from the group consisting of collagen monomer, collagen oligomers, extracellular matrix enzymes, cross-linking agents, immunosuppressive agents, proteoglycans, glycosaminoglycans, hyaluronic acid, glycoproteins, fibronectin, elastin, fibrinogen, thrombin, thrombospondin, silk, growth factors, glucose, heat shock proteins, L-arginine, L-glutamine, polyarginine, polyglutamine, and anionic polymers.
20. The method of item 18, wherein the step of administering comprises the use of a wearable device comprising an infusion pump, a reservoir containing the remodeling solution, a catheter implanted at the tissue remodeling site, and a control module programmed to perform the administering in accordance with said program.
21. The method of item 2, wherein the collagen is atelo-collagen, telo-collagen, pro-collagen, or a mixture thereof.
22. The method of item 2, wherein the collagen is Type I, Type II, Type III, Type IV, Type V, or Type XI.
23. The method of any of the preceding items, wherein the subject is a fish, amphibian, reptile, bird, or mammal.
24. The method of item 23, wherein the subject is a mammal and the mammal is a human.
25. The method of any of the preceding items, further comprising the step of:
    (a0) prior to step (a), implanting an internal sheath into the subject, the sheath surrounding the tissue remodeling site.

26. The method of item 25, wherein the sheath comprises one or more components selected from the group consisting of collagen, proteoglycans, glycosaminoglycans, glycoproteins, fibronectin, fibrin, elastin, silk, cross-linking reagents, and biodegradable polymers.

27. The method of item 25, wherein the tissue remodeling solution is administered through the sheath to reach the tissue remodeling site.

28. The method of item 25, wherein the sheath mimics the stiffness of tendon.

29. The method of item 25, wherein the sheath forms a junction with tendon, ligament, or bone enclosing both ends of a break or tear of the tendon, ligament, or bone, or enclosing a site of damage in the tendon, ligament, or bone.

30. The method of any of the preceding items, further comprising the steps of:
 (c) monitoring one or more parameters in a sample of extracellular fluid obtained from the tissue remodeling site; and
 (d) adjusting the administration or composition of the remodeling solution based on said one or more parameters.

31. The method of item 30, wherein said monitoring comprises using one or more sensors to determine a concentration of a component of said extracellular fluid sample.

32. The method of item 30, wherein said adjusting comprises switching the composition and/or administration of the tissue remodeling solution from support of a collagen growth mode to support of a collagen reconstruction mode, or from support of a collagen reconstruction mode to support of a collagen growth mode.

33. The method of any of the preceding items, wherein the number, diameter, length, density, and/or alignment of collagen fibrils is increased.

34. The method of any of the preceding items, wherein realignment of existing collagen fibrils at the tissue remodeling site is achieved.

35. The method of any of the preceding items, wherein an increase in the number or density of collagen fibrils at the tissue remodeling site is achieved.

36. The method of any of the preceding items, wherein repair of a strain, sprain, tear, or rupture of a tendon or ligament is achieved.

37. The method of item 36, wherein the ligament is an anterior cruciate ligament (ACL), medial cruciate ligament (MCL), posterior cruciate ligament (PCL), lateral collateral ligament (LCL), ulnar collateral ligament.

38. The method of item 36, wherein the tendon is an Achilles tendon, extensor tendon of the hand, flexor tendon of the hand, rotator cuff tendon, or elbow tendon.

39. The method of any of the preceding items, wherein healing of a fractured or broken bone is achieved.

40. The method of item 39, wherein the tissue remodeling solution comprises one or more components selected from the group consisting of calcium, calcium donors; phosphate, phosphate donors; bone-associated non-collagenous proteins such as osteospontin, osteonectin, osteocalcin, phosphophryn, and bone sialoprotein; bone morphogenetic proteins; and synthetic chaperone molecules such as polyaspartic acid.

41. The method of any of the preceding items, wherein the method is applied following surgical repair of a torn or severed tendon or ligament, or a broken bone.

42. The method of any of the preceding items, wherein the method is applied in connection with orthopedic surgery, arthroplasty, orthodontic surgery, vascular surgery, cosmetic surgery, or skin surgery.

43. The method of any of the preceding items, wherein the method is applied to treat chronic back pain, prolapsed or herniated vertebral disc, sports injury, osteoarthritis, rheumatoid arthritis, osteoporosis, keratoconus, glaucoma, or a cartilage disease.

44. The method of any of the preceding items, wherein the tissue remodeling site is a wound.

45. The method of item 43, wherein the method promotes scarless wound healing or reduces scar formation during wound healing.

46. The method of any of the preceding items, wherein a natural healing process is accelerated.

47. The method of any of the preceding items which is performed using the device of item 48.

48. A device for promoting tissue remodeling in a subject in need thereof, the device comprising:
 (i) a dispensing module, comprising:
  a reservoir for a tissue remodeling solution;
  an infusion pump for transporting the tissue remodeling solution from the reservoir;
 (ii) a delivery catheter for transporting the tissue remodeling solution from the infusion pump to a tissue remodeling site in the body of the subject; and
 (iii) a programmable control module for controlling the pump and optionally the composition of the tissue remodeling solution, wherein the control module is programmed to control tissue remodeling by regulating delivery and/or composition of the tissue remodeling solution to the tissue remodeling site, so as to promote collagen fibril assembly, fusion, disassembly, and/or realignment at the tissue remodeling site.

49. The device of item 48, wherein the dispensing module further comprises:
 one or more additional reservoirs for one or more additional reagent solutions, and
 a mixing system for mixing the one or more additional reagent solutions with the tissue remodeling solution prior to its transport to the tissue remodeling site.

50. The device of item 49, wherein the mixing system is a microfluidic chip.

51. The device of item 49 or item 50, wherein the programmable control module controls the mixing of said one or more reagent solutions with the tissue remodeling solution.

52. The device of any of items 49-51, wherein the programmable control module controls the pH, ionic strength, and/or temperature of the tissue remodeling solution and/or the one or more reagent solutions.

53. The device of any of items 48-52, further comprising:
 (iv) a return catheter for transporting extracellular fluid from the tissue remodeling site back to the device for analysis.

54. The device of item 53, wherein the return catheter comprises a filter to exclude cells and assembled fibers.

55. The device of item 53 or item 54, further comprising:
 (v) a sensor for detecting a concentration of one or more components of extracellular matrix fluid at the tissue remodeling site, the sensor providing an output related to the one or more components to the control module.

56. The device of item 55, wherein the sensor is a microcalorimeter.

57. The device of item 55 or item 56, wherein the sensor detects the concentration of collagen.

58. The device of any of items 55-57, wherein the sensor detects the concentration of two or more different species of collagen.

59. The device of any of items 55-58, comprising two or more sensors detecting the concentrations of two or more different components of the extracellular matrix fluid.
60. The device of any of items 55-59, wherein the dispensing module further comprises a mixing system for mixing the returned extracellular fluid with the tissue remodeling solution and/or with one or more additional reagents for transport to the tissue remodeling site through the delivery catheter.
61. The device of item 60, further comprising a microdialysis module for conditioning of returned extracellular fluid before it is transported back to the tissue remodeling site.
62. The device of any of items 48-61, further comprising a temperature control mechanism for controlling the temperature of the tissue remodeling solution and optionally one or more additional reagent solutions stored in the dispensing module or in another module connected with the dispensing module.
63. The device of item 62 that provides both cooling for long-term storage of reagents and warming to body temperature of solutions prior to administration to the subject.
64. The device of any of items 48-63 configured as a wearable device.
65. The device of any of items 48-64 further comprising one or more valves.
66. The device of any of items 48-65, wherein the control module is remote from dispensing module.
67. The device of item 66, wherein the control module is a cell phone, computer, or other wireless device that transmits and receives signals to and from the dispensing module.
68. The device of any of items 48-67 comprising said tissue remodeling solution, and optionally one or more additional solutions, in one or more reservoirs of the dispensing module.
69. The device of any of items 48-68 further comprising one or more additional catheters for administration of the tissue remodeling solution at different locations at or near the tissue remodeling site.
70. The device of any of items 48-69, wherein the delivery catheter comprises a needle for administration of the solution by injection at or near the tissue remodeling site.
71. The device of any of items 48-70, wherein bidirectional flow of tissue remodeling fluid is provided, to and from the dispensing module.
72. The device of item 71, wherein bidirectional flow is provided by reversible flow through the delivery catheter.
73. The device of item 71, wherein bidirectional flow is provided by the combined action of the delivery catheter and a return catheter.
74. The device of any of items 71-73, wherein extracellular fluid collected from tissue remodeling site is collected in a fluid chamber for analysis.
75. The device of any of items 48-74, further comprising a muscle stimulation module that provides electrical stimulation of one or more muscles of the subject in the area surrounding the tissue remodeling site.
76. The device of any of items 48-74, further comprising a passive motion device that provides extensional strain in the area surrounding the tissue remodeling site.
77. A kit comprising the device of any of items 48-76, a tissue remodeling solution, and optionally one or more reagent solutions for use with the device.
78. A kit comprising the device of any of items 48-77 and one or more sheaths for use with the device.
79. An in vitro method of producing one or more collagen fibrils, the method comprising the steps of:

(a) providing a collagen solution initially devoid of collagen fibrils; and
(b) inducing strain in the solution, whereby collagen from the solution assembles into one or more collagen fibrils.
80. The method of item 79, wherein the pH, ionic strength, temperature, and/or collagen concentration of the collagen solution remain essentially constant.
81. The method of item 79, wherein the pH, ionic strength, temperature, and/or collagen concentration are initially low enough to prevent collagen fibril formation and are raised prior to, during, or after inducing strain.
82. The method of any of items 79-81, wherein the collagen solution comprises a mixture of collagen monomers and oligomers.
83. The method of item 82, wherein the collagen solution further comprises collagen aggregates and/or fibrils.
84. The method of any of items 79-83, wherein the collagen solution comprises a total collagen concentration in the range from about 0.001 mg/mL to about 50 mg/mL.
85. The method of any of items 79-84, wherein the collagen is atelo-collagen, telo-collagen, pro-collagen, or a mixture thereof.
86. The method of any of items 79-85, wherein the collagen is Type I, Type II, Type III, Type IV, Type V, or Type XI.
87. The method of any of items 79-86, wherein the collagen solution further comprises one or more components selected from the group consisting of extracellular matrix enzymes, cross-linking agents, pH modifying agents, ionic strength modifying agents, osmicants, plasticizers, fibroblasts, mesenchymal stem cells, cell migration promoters, collagen fibril fragments, proteoglycans, glycosaminoglycans, hyaluronic acid, glycoproteins, fibronectin, elastin, fibrinogen, thrombin, thrombospondin, silk, and growth factors.
88. The method of item 87, wherein the collagen solution comprises a cross-linking agent selected from transglutaminase, lysyl oxidase, glutaraldehyde, paraformaldehyde, and riboflavin.
89. The method of any of items 79-88, wherein extensional strain is induced in the collagen solution at a constant rate, at an increasing or decreasing rate, cyclically, or intermittently.
90. The method of item 89, wherein the extensional strain rate is from about 0.001 $\sec^{-1}$ to about 10 $\sec^{-1}$.
91. The method of item 89 or item 90, wherein collagen fibril assembly is stimulated by flow-induced crystallization.
92. The method of item 79, wherein the strain is held static.
93. The method of item 92, wherein the strain is from 0 to about 2.
94. The method of item 92 or item 93, wherein collagen fibril assembly is stimulated by incorporation of collagen monomers and/or oligomers into pre-existing collagen fibrils.
95. The method of any of items 79-94, wherein extensional strain is achieved by establishing flow or shear in the collagen solution, by pulling the surface of the solution, or by pulling on a collagen fibril in the solution.
96. The method of item 95, wherein a draw probe is used to induce extensional strain.
97. A method for producing an artificial tissue scaffold, the method comprising the step of performing the method of any of items 79-96 while the collagen monomer solution is in a mold, wherein the shape of the mold provides the shape of the tissue scaffold.
98. A method to aid in preventing injury or tissue damage in a subject in need thereof, the method comprising the steps of:

(a) administering to a tissue remodeling site in the subject a tissue remodeling solution, wherein the tissue remodeling site is suspected of being subject to future injury or tissue damage; and (b) inducing strain or an extensional strain rate at the tissue remodeling site, whereby collagen fibril assembly, collagen fibril fusion, and/or collagen fibril disassembly is stimulated at the tissue remodeling site.

99. The method of item 98, wherein the tissue remodeling solution comprises a mixture of collagen monomers and/or oligomers and is devoid of collagen fibrils.

100. The method of item 98, wherein the tissue remodeling solution comprises collagen monomers, dimers, trimers, aggregates, and/or fibrils.

101. The method of any of items 98-100, wherein the tissue remodeling solution further comprises one or more components selected from the group consisting of extracellular matrix enzymes, cross-linking agents, immunosuppressive agents, pH modifying agents, ionic strength modifying agents, osmicants, plasticizers, fibroblasts, mesenchymal stem cells, cell migration promoters, collagen fibril fragments, proteoglycans, glycosaminoglycans, hyaluronic acid, glycoproteins, fibronectin, elastin, fibrinogen, thrombin, thrombospondin, silk, and growth factors.

102. The method of item 101, wherein the one or more factors that delay collagen assembly are selected from the group consisting of glucose, heat shock proteins, L-arginine, L-glutamine, polyarginine, polyglutamine, and anionic polymers.

103. The method of item 101 or item 102, wherein the tissue remodeling solution comprises a cross-linking agent selected from transglutaminase, lysyl oxidase, glutaraldehyde, paraformaldehyde, and riboflavin.

104. The method of any of items 101-103, wherein the tissue remodeling solution comprises an extracellular matrix enzyme selected from matrix metalloproteinases (MMPs), cathepsins, bacterial collagenases, and gagases, such as chondroitinase or hyaluronidase.

105. The method of any of items 101-104, wherein the tissue remodeling solution comprises an immunosuppressive agent, and the immunosuppressive agent is an anti-inflammatory agent.

106. The method of any of items 98-105, wherein the tissue remodeling solution further comprises one or more factors that delay collagen assembly or increase a collagen solubility limit.

107. The method of any of items 98-106, wherein the collagen is atelo-collagen, telo-collagen, pro-collagen, or a mixture thereof.

108. The method of any of items 98-107, wherein the collagen is Type I, Type II, Type III, Type IV, Type V, or Type XI.

109. The method of any of items 98-108, wherein the strain rate is cyclic, intermittent, extensional, or compressive at the tissue remodeling site and the rate is about 0.001 sec$^{-1}$ to about 10 sec$^{-1}$.

110. The method of any of items 98-109, wherein strain is held static and is from 0 to about 2.

111. The method of any of items 98-110, wherein extensional or compressive strain is achieved by physical therapy, massage, stretching, an exercise program, electrical muscle stimulation, or a continuous passive motion device.

112. The method of any of items 98-111, wherein the tissue remodeling solution is administered by one or more injections.

113. The method of any of items 98-112, wherein administering the tissue remodeling solution is performed according to a program that determines the composition or amount of the tissue remodeling solution to be administered and the timing of administering the tissue remodeling solution.

114. The method of item 113, wherein the program determines the presence or absence and concentration (if present) of one or more components of the tissue remodeling solution selected from the group consisting of collagen monomer, collagen oligomers, extracellular matrix enzymes, cross-linking agents, immunosuppressive agents, proteoglycans, glycosaminoglycans, hyaluronic acid, glycoproteins, fibronectin, elastin, fibrinogen, thrombin, thrombospondin, silk, growth factors, glucose, heat shock proteins, L-arginine, L-glutamine, polyarginine, polyglutamine, and anionic polymers.

115. The method of item 113 or item 114, wherein the step of administering comprises the use of a wearable device comprising an infusion pump, a reservoir containing the remodeling solution, a catheter implanted at the tissue remodeling site, and a control module programmed to perform the administering in accordance with said program.

116. The method of any of items 98-115, whereby scar formation at the tissue remodeling site is prevented.

117. The method of any of items 98-116, which is performed in conjunction with a surgical procedure.

118. A method of treating a tumor in a subject, the method comprising the steps of:

(a) administering to a tissue remodeling site in the subject a tissue remodeling solution, wherein the tissue remodeling site comprises said tumor; and (b) controlling the amount of strain induced in collagen at the tissue remodeling site, whereby collagen fibril disassembly occurs in the tumor.

119. The method of item 118, wherein the remodeling solution comprises one or more enzymes acting on components of extracellular matrix.

120. The method of item 118, wherein the one or more enzymes are selected from the group consisting of proteases, collagenases, elastases, matrix metalloproteinases, and hyaluronidases, 121. The method of any of items 118-120, wherein the tumor is monitored and the composition and/or administration of the remodeling solution is adjusted so as to favor further dissolution of the tumor.

122. A tissue remodeling solution comprising:

monomeric collagen, oligomeric collagen, and one or more components selected from the group consisting of extracellular matrix enzymes, cross-linking agents, immunosuppressive agents, pH modifying agents, ionic strength modifying agents, osmicants, plasticizers, fibroblasts, mesenchymal stem cells, cell migration promoters, collagen fibril fragments, proteoglycans, glycosaminoglycans, hyaluronic acid, glycoproteins, fibronectin, elastin, fibrinogen, thrombin, thrombospondin, silk, and growth factors.

123. The tissue remodeling solution of item 122, wherein the collagen is Type I, Type II, Type III, Type IV, Type V, or Type XI.

124. The tissue remodeling solution of item 122 or item 123 that comprises collagen monomers and/or oligomers and is devoid of pre-existing collagen fibrils.

125. The tissue remodeling solution of item 122 or item 123, wherein the tissue remodeling solution comprises collagen monomers, dimers, trimers, aggregates, and/or fibrils.

126. The tissue remodeling solution of any of items 122-125, wherein the tissue remodeling solution further comprises one or more factors that delay collagen assembly or that increase a collagen solubility limit.

BRIEF DESCRIPTION OF THE DRAWINGS

FIG. 4A) A fiber drawn from a droplet of collagen solution demonstrates the high aspect ratio of fibers that can be created. FIGS. 4B-4D) Cross-sectional schematics of the collagen droplet and surrounding environment at different time points. FIG. 4B) Dry nitrogen gas was passed above the droplet to facilitate evaporation from the droplet surface. FIG. 4C) After 120 sec, an enriched monomeric surface was produced as a result of the water molecules exiting the droplet faster than the collagen molecules could diffuse into the bulk (estimated Péclet number (Pe) was 2.15). At this point a collagen fiber could be drawn from the droplet. FIG. 4D) A glass needle was used to pierce the droplet surface and then drawn outward by 150 sec. As the meniscus of the droplet drained from the needle, a collagen fiber persisted. FIG. 4E) The fiber formation process was triggered by the applied extensional strain caused by pulling the needle away from the droplet. The upper image shows the aligned fibrils being drawn into the fiber. The image below shows a magnification of the white box. Here it is clearly visible that the fibrils only begin in response to the mechanical stimulation. The white arrowheads denote where the extensional rate reached the critical value required to initiate fibrillogenesis. FIGS. 4F-4I) The image sequence demonstrates the repair of a collagen fiber. The end of the collagen fiber segment was identified by the white arrow. The fiber segment end was placed into the droplet and drawn out, initiating a repair site and the continuation of new fiber formation.

FIGS. 6A-6F show images of drawn collagen fibers. The midsection of fibers pulled from solutions of (FIG. 6A) atelo-collagen and (FIG. 6B) telo-collagen, observed under phosphate buffer. FIG. 6C) Drawing a fiber from a pre-polymerized droplet of telo-collagen (held under silicone oil to prevent evaporation and maintain pH and ionic strength). Pre-assembled collagen fibrils adhered to a glass microneedle and allowed a fiber to be drawn from the assembled network. The arrows identify the location from where the fiber was drawn. FIG. 6D) The midsection of the fiber drawn from the pre-formed collagen network clearly presented the disorganization and poor spatial packing that results from pulling out an entangled network. The fiber morphology was far different than that observed in FIG. 6A or FIG. 6B, which indicated that triggering polymerization via extensional strain was a uniquely different process than drawing a fiber from an already formed network. This observation suggests that even cellular manipulation of an already polymerized network is unlikely to result in highly-aligned fibrillar structures without further modification. Transmission electron microscope (TEM) images of the (FIG. 6E) atelo- and (FIG. 6F) telo-collagen droplet surface (preserved by quick freezing then replicated following deep-etching by rotary shadowing with platinum) at the time when a fiber would be drawn (150 seconds). Generally, the surfaces of the collagen droplet were enriched with a high concentration of monomers that have not yet assembled into larger hierarchical structures.

FIGS. 7A-7C depict the structure of a drawn telo-collagen fiber at progressively increasing magnification. FIGS. 7D-7F similarly depict a drawn telo-fiber from a solution that contained 2% decorin. Both fibers displayed an impressive hierarchal morphology reminiscent of native tendon. However, the effect of the addition of decorin (a small leucine rich proteoglycan found in the ECM, known to affect collagen fibril morphology) was apparent at the level of the individual collagen fibrils (FIG. 7C—no decorin vs. FIG. 7F—with decorin). As seen in vivo, decorin appears to reduce the number of lateral associations between the fibrils in vitro as well.

FIGS. 8A-8F show images of TEM thin sections of drawn atelo-fibers showing their typical shell, transition, and core structure. FIG. 8A) The longitudinal section of the fiber depicts the peripheral shell of highly-organized fibrils and the poorly organized core of the fiber. FIG. 8B) The striking alignment of fibrils in the shell, in the direction of the applied strain, was highly mimetic of native tendon morphology. FIG. 8C) High magnification of the rectangular region (outlined in image of FIG. 8B) shows the discrete, uniform diameter, consistent spacing, and continuous nature of the fibrils in the shell where the extensional strain was highest. FIG. 8D) The transition from high density, continuous fibrils to randomly arranged, sparse, shorter fibrils was sometimes abrupt (typically in thinner regions of the fiber). FIG. 8E) In sections of fibers with a larger diameter (>20 micrometers), a transitional region was present, comprising short and wavy fibrils that were oriented in the general direction of the extensional strain. FIG. 8F) The core of the fibril comprised discrete, isotropic fibrils with low spatial density.

FIGS. 9A-9H show how a collagen concentration gradient along the depth of the droplet surface and varying extensional strain regimes during fiber drawing account for the multiphase fiber morphology seen in the TEM images. FIGS. 9A, 9B) Images during the drawing of a telo-fiber with fluorescent beads in the solution. The fluorescent bead highlighted in red remained stagnant, while the bead highlighted in blue accelerated along the hyperbolic geometry and entered the fiber. The full video identified a recirculation zone at the base of the necking region, which explains the isotropic fiber core morphology. FIG. 9C) This schematic characterizes the rheological flow regimes in the necking region, based on fluorescent particle velocity profiles and concentration measurements throughout the droplet. The highest extensional strain, ~1 $sec^{-1}$, was achieved on the surface of the droplet, and the corresponding structure (I) shown in FIG. 9D comprised highly aligned, FIC telo-collagen fibrils. Just below the surface, the collagen concentration was lower and the flow had shear component which yielded angled, disrupted fibrillar morphology (II). In the transitional region, the rotational component of the flow increased and the further decreased collagen concentration produced a swirling morphology (III) shown in FIG. 9E. At the core of the necking region, the concentration was approximately that of the bulk concentration, 4.5 mg/ml, and the resulting fiber morphology (IV) seen in FIG. 9F was an isotropic matrix. The concentration/viscosity gradient disrupted the pure extensional flow below the surface, but the favorable molecular response to extensional strain was evident at the fiber shell. The molecular positioning within the fibrils was also investigated using TEM. FIG. 9G) Fibrils with the native banding pattern were prevalent. FIG. 9H) The bracketed region in FIG. 9G was analyzed using power spectral analysis to measure the banding periodicity, and the dominant frequency correlated to a 65.5 nm banding periodicity.

DETAILED DESCRIPTION OF THE INVENTION

Figure 1:
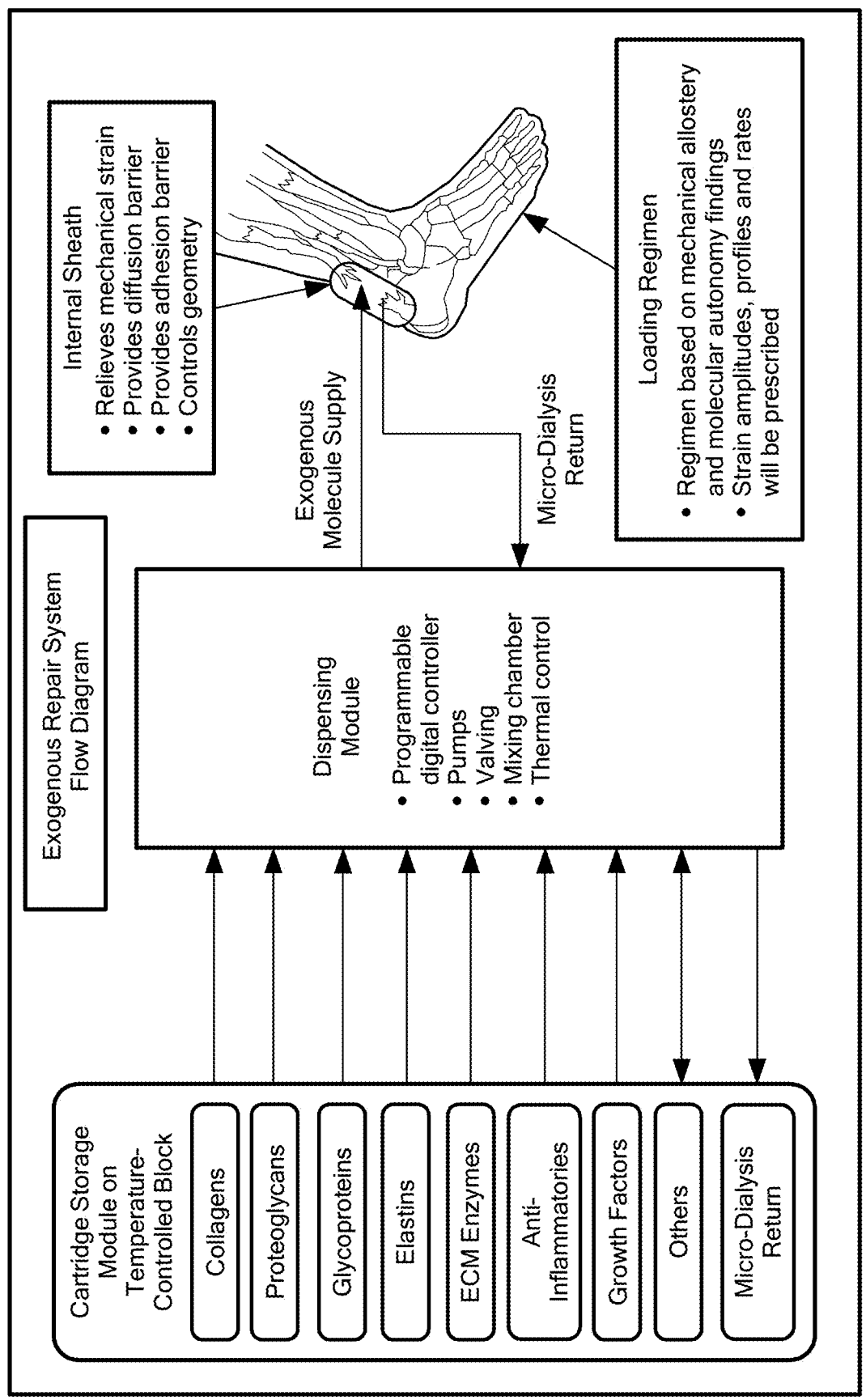
FIG. 1 shows a schematic illustration of a method to aid in remodeling of a collagenous tissue.

While a number of factors are known to affect collagen assembly in vitro, it was previously unknown how the organization of collagen fibrils is created and maintained in vivo, and this lack of knowledge has hindered efforts to enhance natural healing processes for serious injuries such as ruptured ligaments and tendons and fractured bones, Now, according to the present invention, collagen fibers can be assembled from monomeric collagen using only mechanical strain, and the resulting fibers spontaneously align to provide stabilization against extensional or compressive strain. This collagen assembly process is believed to function by a flow induced crystallization mechanism analogous to similar mechanisms encountered in polymerization reactions.

Strain-induced assembly of collagen serves as the foundation of a novel method for triggering and managing collagen fibril formation in vivo with consequent reorganization and remodeling of extracellular matrix tissue and collagen-containing structures therein. The method can be used to remodel any type of collagenous tissue. Collagenous tissues suitable for application of the invention include any bone, cartilage, tendon, or ligament found in an animal body, as well other tissues or organs attached to or surrounded by a collagenous tissue, such as skeletal, cardiac, and smooth muscle, and tissues or organs containing a significant fraction of extracellular matrix containing fibrillary or other forms of collagen. As used herein, collagen refers to a protein having triple helical structure and an amino acid sequence characterized by a repeated gly-x-y motif, where x is frequently proline and y is frequently hydroxyproline. Collagen for use in the invention can have all or part of C-terminal and/or N-terminal telopeptides (referred to herein as "telo-collagen"), as well as all or part of C-terminal and/or N-terminal propeptides (referred to herein as "pro-collagen"). Collagen lacking the propeptides (referred to as "collagen") as well as collagen lacking the telopeptides (referred to herein as "atelo-collagen) also can be used. Fibril-forming collagens such as Type I, Type II, Type III, Type V, or Type XI collagen are preferred, although other types of collagen including Type IV also can be used.

Methods of the invention provide tissue remodeling in a collagenous tissue. Such remodeling includes repair of ruptured or torn structures containing a high density of closely packed collagen fibers, such as tendons or ligaments. Remodeling according to the invention also includes repair, strengthening, enlargement, and/or realignment of individual collagen fibrils or fibers, and also can include partial or complete disassembly or degradation of collagen fibrils or fibers. Preferably, tissue remodeling according to the invention closely mimics and attempts to recreate or restore the natural tissue organization resulting from development, but it may also include strengthening various structures of the body, such as ligaments or tendons, beyond their natural state so as to prevent future injury or damage. tissue remodeling solution. The site at which such tissue remodeling is targeted is referred to herein as the "tissue remodeling site", which may include some surrounding tissue adjacent to an injury.

The invention provides a method of promoting collagenous tissue remodeling in a subject in need thereof. The method includes the steps of: (a) administering to a tissue remodeling site in the subject a tissue remodeling solution; and (b) inducing strain or strain rate at the tissue remodeling site, whereby collagen incorporation, collagen fibril assembly, or collagen fibril disassembly is stimulated at the tissue remodeling site. A representation of the method is provided in FIG. 1. Although the induction of mechanical strain at the tissue remodeling site is key to stimulating the growth and/or remodeling of collagen fibers in the tissue, the remodeling site typically lacks sufficient ECM cells, such as fibroblasts, to produce sufficient collagen monomers and other required structural proteins and enzymes to support rapid growth, healing, and particularly wound repair. Therefore, the relative deficiency of such soluble components can be overcome by administration of a tissue remodeling solution to the remodeling site.

As used herein, a "tissue remodeling solution" refers to a solution containing soluble "pre-fibrillar" collagen molecules and optionally includes one or more other substances that promote or regulate the assembly, incorporation, fusion, and/or disassembly and degradation of collagen fibrils. Any of the above named species of collagen molecules can be included in the remodeling solution; however, collagen molecules in monomeric form (collagen monomers) are strongly preferred as a major component of the solution. Other pre-fibrillar forms of collagen may also be included, such as dimeric collagen or oligomeric collagen (soluble collagen associated into complexes of two or more collagen molecules), or even fragments of collagen fibrils or fibers, which can readily be obtained by enzymatic or chemical treatment of collagen isolated from animal tissues. Collagen molecules or fibrillar fragments used in the remodeling solution are preferably of the same species on which the solution is to be used, but also can be from another species. For example, bovine collagen can be used to treat humans due to its low immunogenicity. The tissue remodeling solution can be provided as a single solution, or it can be mixed from two or more reagent solutions shortly before administration. Preferably, the tissue remodeling solution comprises a total collagen concentration in the range from about 0.001 mg/mL to about 50 mg/mL, or about 0.01 mg/mL to about 50 mg/mL, or about 0.1 mg/mL to about 50 mg/mL, or about 1 mg/mL to about 50 mg/mL, or about 5 mg/mL to about 50 mg/mL, or about 10 mg/mL to about 50 mg/mL, or about 1 mg/mL to about 30 mg/mL, or about 10 mg/mL to about 20 mg/mL, or about 15 mg/mL.

Optional additions to the tissue remodeling solution include additional structural or accessory proteins, enzymes, small molecules, and ionic species that interact with collagen or assist in regulating collagen assembly, disassembly, or organization processes. For example, the remodeling solution can include one or more of: extracellular matrix enzymes, cross-linking agents, immunosuppressive agents, pH modifying agents, ionic strength modifying agents, osmicants, plasticizers, fibroblasts, mesenchymal stem cells, cell migration promoters, collagen fibril fragments, proteoglycans, glycosaminoglycans, hyaluronic acid, glycoproteins, fibronectin, elastin, fibrinogen, thrombin, thrombospondin, silk, and growth factors.

Extracellular matrix enzymes can be added to degrade or polymerize collagen or non-collagen fibrils or macromolecules of the ECM, such as proteoglycans and glycosaminoglycans. For example, ECM enzymes can be matrix metalloproteinases (MMPs), cathepsins, bacterial collagenases or other collagenases, and gagases, such as chondroitinase or hyaluronidase.

Cross-linking agents include enzymes or chemical reagents that from covalent lateral cross-bridges between adjacent collagen molecules in a fibril, so as to strengthen and stabilize the fibril. Suitable cross-linking agents include, for example, enzymes such as transglutaminase or lysyl oxidase, or chemical cross-linkers such as glutaraldehyde, paraformaldehyde, or riboflavin.

Immunosuppressive agents can be added to modify immune system functions, such as inflammation, which can have an inhibitory effect on wound healing or tissue remodeling, and can cause the egress of ECM cells that are important to the remodeling process. Suitable immunosuppressive agents include a variety of anti-inflammatory agents, such as non-steroidal anti-inflammatory drugs (NSAIDS), hormones such as cortisone and its derivatives, and a variety of cytokines.

Agents that modify the chemical milieu of the tissue remodeling site can be important to promote conditions, such as pH, ionic strength, and osmolarity, which favor or disfavor collagen assembly or disassembly. pH modifying agents include acids and bases as well as pH buffers, and nontoxic varieties are well-known in the art. Agents that modify ionic strength include salts, which preferably provide ionic species such as sodium, potassium, and chloride ions that are prevalent in the extracellular space and used at levels which do not cause cellular disruption. Osmicants are polymers or macromolecules that generate or increase osmotic pressure and cause water or solution to flow. Suitable osmicants include polyethylene glycol (PEG), proteoglycans, or glycosaminoglycans such as hyaluronic acid and chondroitin sulfate. They can be used at concentrations in the range from 0.1 to 50 wt %, for example.

As used herein, "plasticizers" are substances that delay the assembly of collagen, i.e., that keep collagen soluble and prevent it from forming structures that are too large prior to reaching the remodeling site. As the collagen concentration in the remodeling solution increases, the amount of time before it forms a fully entangled network decreases. The addition of a plasticizer delays fibril assembly by limiting interactions and chaperoning the collagen molecules (or small aggregates of collagen molecules) to the remodeling site. Any molecule that limits the molecular interactions required for collagen assembly or related reactions, e.g., binding of collagen monomers to other monomers, oligomers, or aggregates; assembly; denaturation; or enzymatic reactions, of any component in the remodeling solution with other components in the solution or molecular components present in the in vivo environment at the remodeling site. Examples of suitable plasticizers include glucose, heat shock proteins, L-arginine, L-glutamine, polyarginine, polyglutamine, and anionic polymers.

Further possible components of the tissue remodeling solution include cells such as ECM cells, such as fibroblasts, chondriocytes, or osteoblasts; and mesenchymal stem cells or other stem cells. A similar role can be played by adding cell migration promoters, such as cytokines involved in the inflammation process, which can recruit endogenous ECM cells to the tissue remodeling site. Promoters of cellular differentiation, such as growth factors (e.g., endothelial derived growth factor or fibroblast growth factor) also can be included to promote the growth and development of ECM cells at the tissue remodeling site.

Naturally occurring ECM molecules are also suitable for inclusion in the tissue remodeling solution. Such molecules combine with the accelerated assembly of collagen fibers to promote the regrowth of ECM and structures related to it. Suitable ECM molecules include proteoglycans, glycosaminoglycans such as hyaluronic acid, glycoproteins, fibronectin, elastin, fibrin and fibrinogen.

In some embodiments of the method, an additional step is the implanting of an internal sheath into the subject, wherein the sheath surrounds the tissue remodeling site. The sheath allows the molecules of the tissue remodeling solution to remain in concentrated form near the remodeling site, and to create a local environment or milieu which is suitable for remodeling. The sheath can be a membrane or sack that is permeable or selectively permeable, and is preferably fabricated of a biodegradable polymer or a protein or other biopolymer such as collagen, proteoglycans, glycosaminoglycans, glycoproteins, fibronectin, fibrin, elastin, or silk. The sheath can also include one or more cross-linking reagents or its protein components can be cross-linked prior to implantation.

In some embodiments, the method further includes monitoring one or more parameters in a sample of extracellular fluid obtained from the tissue remodeling site; and adjusting the administration or composition of the remodeling solution based on the parameters. Such monitoring can be supplied by the use of one or more biosensors or chemical sensors that detect molecules of interest, such as collagen monomers, or other proteins, proteoglycans, glycosaminoglycans, or enzymes. Monitoring of pH, ionic strength, and osmotic or oncotic pressure also can be performed. Microcalorimetry also can be performed to provide a measure of the overall concentration of protein or macromolecules at the remodeling site. In response to such monitoring, adjustments can be made in the composition or rate or frequency of administration of tissue remodeling solution so as to achieve a move favorable remodeling outcome.

The tissue remodeling solution can be administered to the tissue remodeling site by any method known in the art. The solution can be administered in a single injection, intermittently, or continuously over a period of time. It can be administered manually by injection directly into the tissue remodeling site, or with the aid of an infusion pump or other pump or automated device.

Strain can be induced at the tissue remodeling site in a number of ways. Preferred methods include the use of physical therapy, massage, stretching, electrical stimulation of muscles (e.g., through use of a TENS device), targeted motion of one or more specific joints or muscles, or an exercise program targeted to provide appropriate strain to the treated area. Biomechanics can be employed to determine an appropriate protocol that provides the required degree of strain to the site. Strain can be applied statically or dynamically. Static strain deforms the remodeling site and maintains a constant deformation for some period of time, although the value of static strain can be changed cyclically or intermittently. Strain rate can be applied by the continuous extension or compression of the remodeling site for a period of time, and strain rate can be applied in a cyclic, intermittent, increasing, or decreasing fashion. A continuous passive motion (CPM) device also can be employed to induce strain at the site of tissue remodeling. Strain rates that are effective for stimulating collagen assembly or disassembly can vary, for example, from about 0.001 $\sec^{-1}$ to about 10 $\sec^{-1}$, or from about 0.01 $\sec^{-1}$ to about 10 $\sec^{-1}$, or about 0.1 $\sec^{-1}$ to about 10 $\sec^{-1}$, or from about 0.01 $\sec^{-1}$ to about 5 $\sec^{-1}$, or about 0.1 $\sec^{-1}$ to about 5 $\sec^{-1}$, or from about 1 $\sec^{-1}$ to about 5 $\sec^{-1}$, or from about 0.1 $\sec^{-1}$ to about 2 $\sec^{-1}$, or from about 2 $\sec^{-1}$ to about 5 $\sec^{-1}$.

A result of the method is in most cases to stimulate collagen fibril formation at the tissue remodeling site through the use of the remodeling solution combined with induced strain, and through the use of appropriately induced strain to align new and pre-existing collagen fibrils in a direction that stabilizes the tissue against strain induced during everyday activities or stressful activities, including work and sports activities. Thus, the method can result in an increased number of collagen fibrils, or larger fibrils, or fibrils that are better aligned and organized in a suitable direction or combination of directions to stabilize the tissue and restore function to the remodeling site. This can be accomplished not only by de novo collagen fibril assembly, but also by incorporation of supplied (i.e. exogenous) collagen monomers, oligomers, or aggregates into pre-existing collagen fibrils.

The method of the invention can further promote the fusion of collagen fibrils (new or pre-existing, or a combination of new and pre-existing) end to end, resulting in longer fibrils. For example, fibrils can be generated in gaps at a repair site via induced extensional strain rate, but the ends of those fibrils must fuse to either end of endogenous fibrils in the damaged tissue, in order to reestablish a continuous tissue. Fibril fusion is a process that is known to occur spontaneously in an end-to-end fashion when fibril ends are in close proximity to each other. Thus, newly formed fibrils fuse to the existing tissue being repaired to restore continuity.

Another result of the method is to avoid or minimize scar formation in a wound healing process or tissue remodeling process. Scar tissue forms due to a poor control over the mechanics and molecules present at an injury site. The injury causes the poor mechanics, as well as inflammation and production of material by foreign cells (neighbor cells and immune cells). Mechanically unloaded tissue, following an injury, is vulnerable to further degradation. The result is disorganized scar tissue, which is then cross-linked for strength, making an inferior structure more permanent. Using the method of the invention, scar formation can be prevented or reduced in part by reducing inflammation and suppressing the immune system through the use of suitable components of the remodeling solution 4. Scar is then prevented by repairing quickly enough that the typically disorganized endogenous production has less impact on the process. Optionally, the cells' ability to crosslink collagen fibrils at the site too early can be inhibited by adding beta-aminoproprionitrile (BAPN). Remodeling is then procedes by controlling the strain and adding in appropriate enzymes to the remodeling solution to remove the disorganized material.

Figure 2:
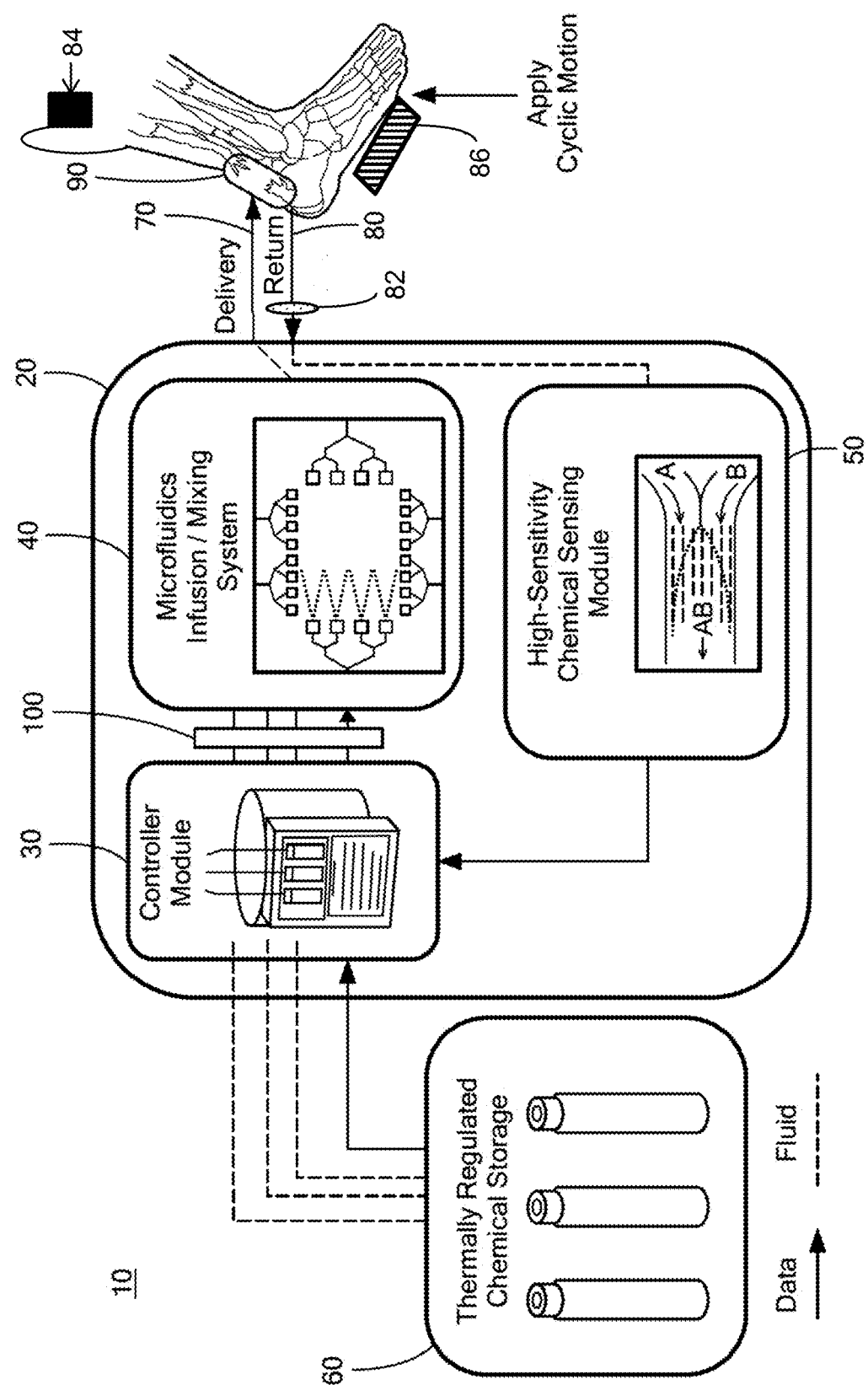
FIG. 2 is a schematic illustration of a device to aid in remodeling of a tissue.

A device for carrying out the method of the invention is depicted in FIG. 2. The device is preferably configured as wearable (e.g., fastened to the skin or worn above clothing), but can be separate from the body in certain situations, such as for a patient immobilized for a period of time. Device 10 includes dispensing module 20, control module 30, one or more chemical storage reservoirs 60 (e.g., at least one reservoir for a tissue remodeling solution), delivery catheter 70 for supplying one or more solutions to the tissue remodeling site, and pump 100. The remaining components, including mixing system 40, sensing module 50, return catheter 80, filter 82, muscle stimulation module 84, passive motion device 86, and sheath 90, are all optional.

The dispensing module contains the one or more solution or reagent reservoirs and the devices or sub-modules needed to deliver the solutions and/or reagents to the tissue remodeling site. One reservoir contains the tissue remodeling solution. Additional reagents contained in other reservoirs can be combined with the remodeling solution to alter its composition as required for treatment. The reservoirs, or the entire dispensing module, can optionally be cooled and/or heating as may be required to preserve the activity of the solutions/reagents. An infusion pump is responsible for delivering the remodeling solution to the tissue remodeling site, and optionally can also be responsible for delivering reagents, remodeling solution, and returned patient fluid to an optional mixing system. The output of the pump is connected to the delivery catheter for transporting the tissue remodeling solution from the infusion pump to a tissue remodeling site in the body of the subject. The control module is responsible for controlling the pump and optional mixing system and temperature control system. The control module preferably can be programmed to provide administration of the tissue remodeling solution at a suitable rate and/or interval, and also to manage the composition of the tissue remodeling solution to promote collagen fibril assembly, disassembly, fusion of fibril ends, and/or realignment of fibrils at the tissue remodeling site. The optional return catheter is used for transporting extracellular fluid from the tissue remodeling site back to the device for analysis. The dispensing module can include a microdialysis sub-module for conditioning of returned extracellular fluid before it is transported back to the tissue remodeling site, or mixed with the tissue remodeling solution for delivery to the remodeling site. The optional sensor module can be used to determine the concentration of one or more components of extracellular matrix fluid at the tissue remodeling site, or of a recirculated tissue remodeling solution. In certain embodiments, the device includes, or is attached to and controls through the control module, a device for automated induction of strain at the tissue remodeling site. Such a strain induction device can be, for example, a muscle stimulation unit, or a passive motion device.

EXAMPLES

Example 1. In Vitro Collagen Fiber Assembly by Induction of Extrinsic Strain

Collagen Preparation

Two bovine, dermal collagen sources were used in the creation of aligned collagen fibers. Pepsin extracted collagen (5010-D, Advanced Biomatrix) and acetic acid extracted collagen (5026-D, Advanced Biomatrix) were used with a starting concentration of 6 mg/ml suspended in 0.01 M HCL. The pepsin extracted collagen was neutralized using an 8:1:1 ratio of collagen, 10× phosphate buffered saline (PBS) (BP399-1, Fisher Scientific), and 0.1 M NaOH (12419-0010, Fisher Scientific) respectively. This resulted in a pH of 7.3. For the experiments using decorin (D8428-.5MG, Sigma Aldrich), a ratio of 2% decorin to collagen molar ratio was used. The 0.5 mg lyophilized decorin was first reconstituted with 1 ml deionized water. To prevent any spontaneous polymerization while working with acetic acid extracted collagen, the neutralization ratio was altered such that the amount of 0.1 M NaOH was increased to 115%. Consequently this resulted in a pH of 7.7. However, no fibrils were detected via differential interference contrast microscopy for twice as long as the experimental time.

Fiber Drawing Setup

Figure 3:
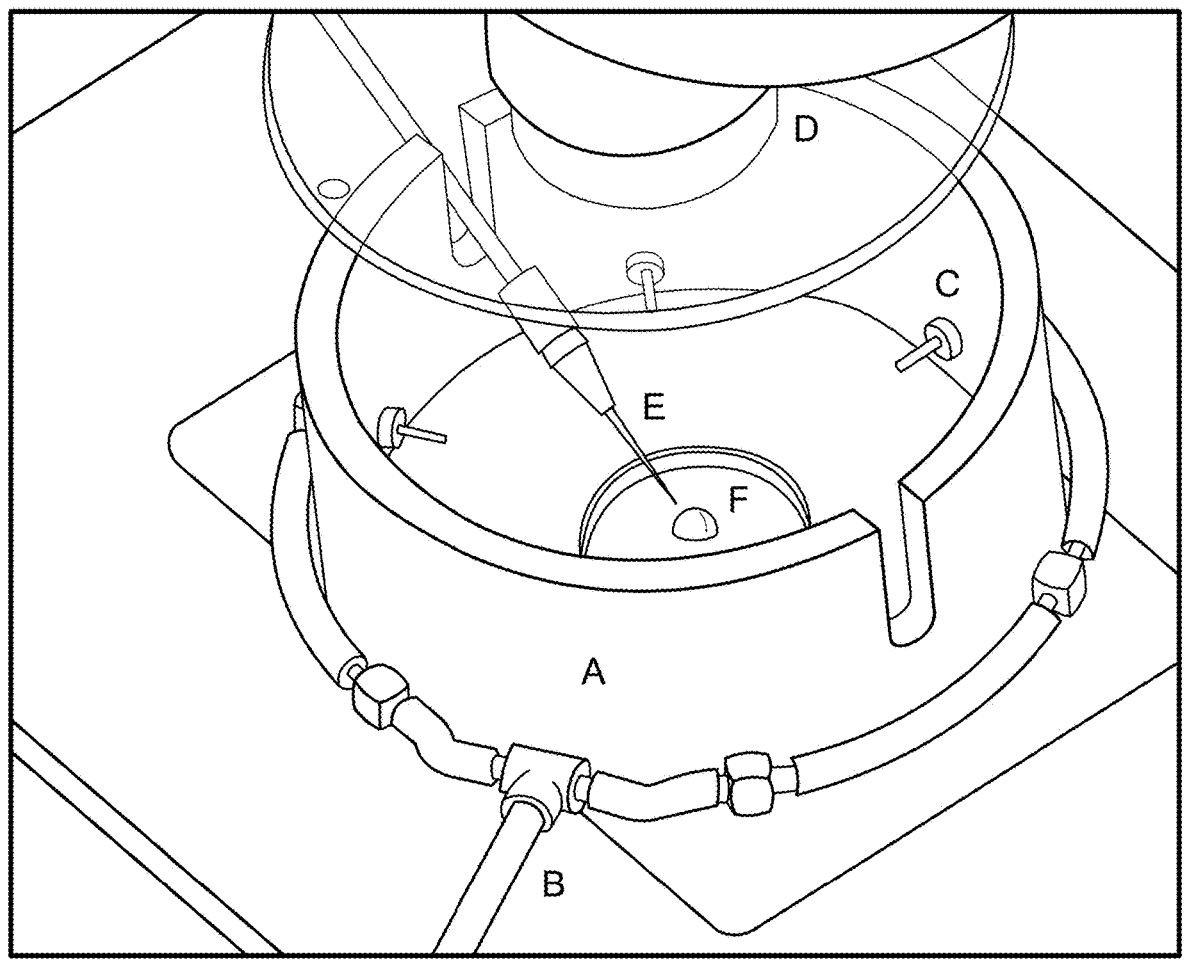
FIG. 3 shows a schematic illustration of an apparatus for drawing a collagen fiber from a collagen solution by extensional strain.

The collagen fiber drawing setup, shown in FIG. 3, was located on a Nikon TE-2000E microscope for live imaging and visual feedback. A custom nitrogen diffusing chamber was designed to provide humidity control and enhance the evaporation rate through convection. A nitrogen tank, regulated to 0.022 psi by a digital pressure controller (PCDAS-1PSIG-D/5P, 5IN, Alicat Scientific), supplied the chamber's one primary inlet that then branched off to six nozzles to provide a constant flow of dry nitrogen gas. A 125 µl droplet of neutralized collagen solution sat on top of an 8 mm glass coverslip, which rested on top of a 40 mm glass coverslip. The 8 mm coverslip was essential for pinning the boundary of the droplet, resulting in a repeatable initial geometry and evaporation profile. The 40 mm coverslip was used to provide the optical access to the inverted microscope. A glass micro-needle, held by a capillary holder and moved by an electronic micromanipulator (TransferMan NK 2, Eppendorf), was used as the probe to draw the collagen fiber. The chamber lid was mounted on the condenser lens of the microscope to isolate the chamber volume from the local humidity in the room.

Fiber Drawing Protocol

Prior to making the neutralized collagen solution, five minutes with the nitrogen gas flowing was allotted to equilibrate the humidity level within the chamber to <5% humidity. The collagen solution was then made by first combining the NaOH and PBS components and lastly adding the collagen component. This reduced the initial pH shock and prevented any instantaneous precipitation. The solution was then pipetted in and out (carefully avoiding introduction of air bubbles)≥15 times to yield a homogeneous, neutralized solution. Next, 125 µl were pipetted onto the 8 mm glass coverslip, again avoiding the addition of any air bubbles. The micro-needle was inserted 500 µm below the surface of the apex of the droplet, and then the system was untouched for 120 seconds. After the allotted time, a pre-written program in NIS Elements AR v4.13 raised the micro-needle as follows:

| Absolute Position (µm) | Velocity (µm/sec) |
| --- | --- |
| 1,500 | 20 |
| 2,500 | 90 |
| 11,500 | 240 |
| 13,500 | 130 |

The initial wait step was required to pull a fiber of appreciable length (>10 mm), and the slower starting velocity was designed to initiate the formation of an attachment that could withstand the release of the meniscus. The 90 µm/sec velocity aided in smoothly transitioning to a 240 µm/sec velocity without breaking the fiber. The 240 um/sec velocity best paired with the speed of the evaporative surface enrichment, such that over the length of the fiber there was little visible thinning or thickening. The final step was included to ramp down the velocity as the source of enriched collagen was also equivalently depleted from the droplet. Once the fiber pull had completed, the fiber was given one minute to dry, before being stored for later analysis.

Calculating the Extensional Strain Rate

The extensional strain rate was calculated by recording the motion of fluorescent, 1.9 µm microspheres (G0200, Thermo Scientific) during the fiber drawing process at 7 frames per second. The position and timestamp of each video frame was used to calculate the 2D velocity magnitude, assumed to be the velocity along the streamline, of an individual bead moving through the necking region of the droplet. The extensional strain rate was then determined as the change in the 2D velocity magnitude divided by the distance the bead moved between each frame. Although the streamline along the necking region was a curved path, the incremental analysis allowed the distance to be approximated as a straight line with minimal error. The extensional strain rate was calculated as 0.39±0.18 s-1.

Touch Freezing and Quick Freeze Deep Etch Sample Preparation

Both atelo- and telo-collagen droplets were subjected to the fiber drawing protocol ~ and were preserved just prior to actually drawing the fiber. The preservation process included mounting the droplet and coverslip on a linear motor (stator #0150-1254 and slider #0150-1524, LinMot), followed by a rapid approach towards a liquid nitrogen cooled copper mirror. The custom touch70 freezer brought the sample to 5 mm above the mirror surface at 2.5 m/s to minimize excessive heat transfer, followed by a final approach at 2 cm/sec to minimize the mechanical distortion. The frozen droplets were stored in liquid nitrogen until they were transferred to the quick freeze deep etch (QFDE) device.

The QFDE device was a modified Cressington freeze fracture system (CFE-40, Cressington Scientific Instruments). The droplets were etched inside the QFDE for 1 hour at $-100°$ C. and $10^{-6}$ torr to remove the vitrified ice from the surface of the droplet. Next the QFDE temperature was reduced to $-130°$ C. to minimize the grain size (1.5-2.5 nm) when depositing both the platinum (~4 nm thick) and carbon (~10 nm thick) layers. The platinum/carbon replica was then isolated from the collagen droplet via a digestion in 25% bleach. After one hour in bleach, the replica was transferred to deionized water for 1 hour. Lastly the replicas were picked up on 600 mesh copper grids and imaged using a JEOL JEM 1010 transmission electron microscope (JEOL, Japan).

Atelo-fiber Preparation for Transmission Electron Microscopy

Atelo-fibers were prepared for transmission electron microscopy (TEM) by incubating for 48 hours at 37° C. in phosphate buffered saline under nominal strain on the microscope (FIGS. 8A-8F) to observe if any visual changes were occurring to the structure of the fibers. The application of strain was used to maintain the fiber within a narrow focal plane for long-term imaging. No visual changes were observed during the incubation, so the fibers were then fixed with a recipe of 2.5% glutaraldehyde and 2.5% paraformaldehyde in a 0.1 M sodium cacodylate buffer for 1 hour at room temperature, followed by three washes, post-fixation with 1% osmium tetroxide in 0.1 M sodium cacodylate buffer for one hour, three washes, and a graded series of ethanol exchanges. Fibers were embedded in resin and then longitudinally thin sectioned on a microtome (Ultracut E, Reichert) using a diamond knife. The ~90 nm thin sections were plated on TEM grids and stained with 5% uranyl acetate and 5% Reynolds lead citrate. The sections were viewed on the TEM and images were digitally captured on a CCD camera system (AMT XR-41B, Advanced Microscopy Techniques Inc.).

Telo-fiber Preparation for Scanning Electron Microscopy

Telo-fibers were prepared for scanning electron microscopy (SEM) by incubating the fibers for 48 hours at 37° C. in phosphate buffered saline in an unloaded, unattached manner. This allowed for parallel processing of the samples, but resulted in significant dissociation of the fibers. When the unloaded incubation was repeated for atelo-fibers, the fibers equivalently dissociated, and it was realized that stabilization (via strain) was essential for uncross-linked fiber persistence at physiological temperature. To maintain a parallel processing approach, polyethylene glycol (MW=20 kDa) was used at physiological concentration[35] for its osmotic stabilizing effects[34] (FIGS. 3A-C), as a substitution to strain-stabilization. Telo-fibers were also processed on the microscope with strain instead of polyethylene glycol (PEG) as a control, but no observable differences were recognized in the fiber morphology.

Figures 7A, 7B, 7C:
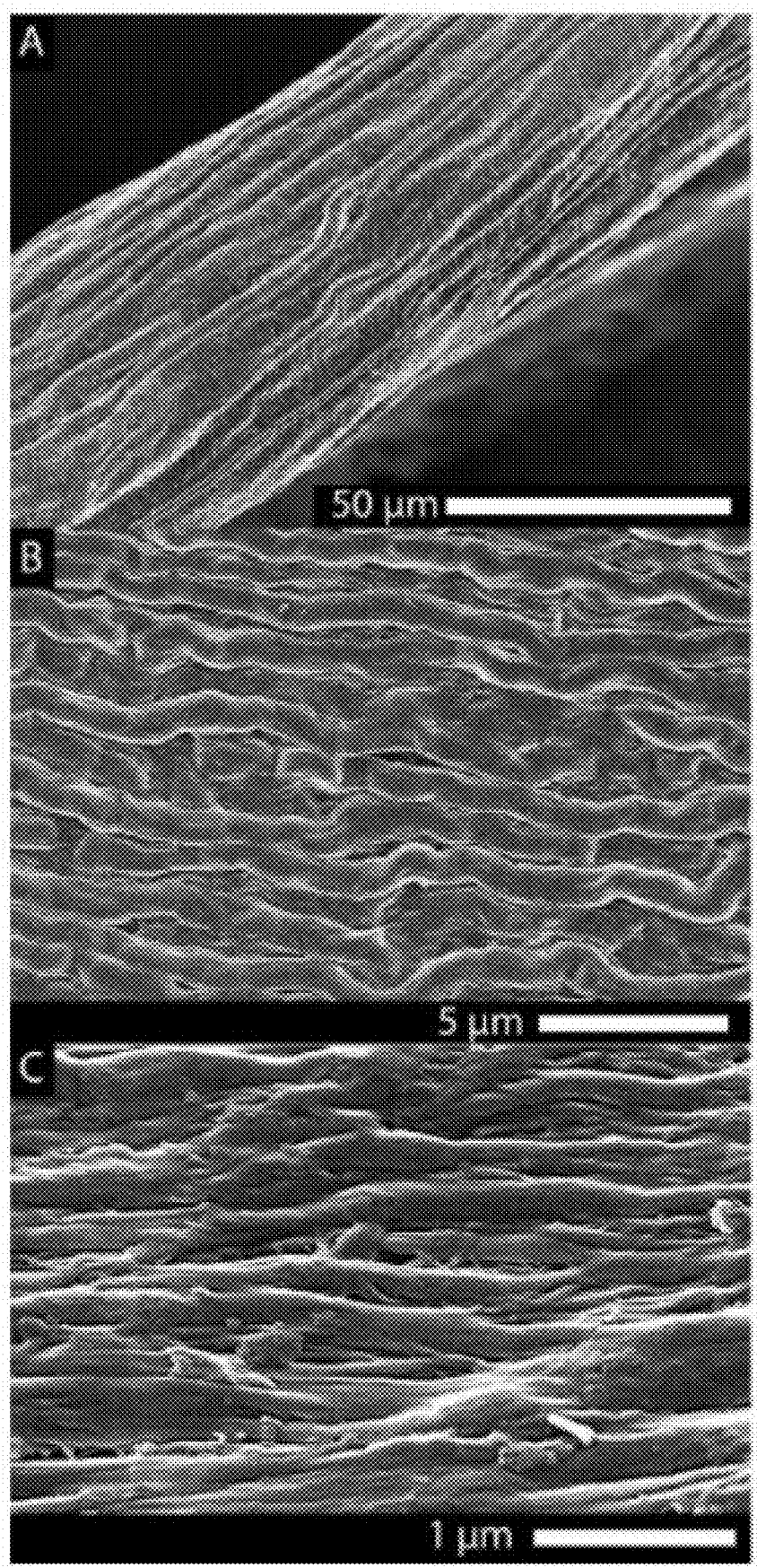
FIGS. 7A-7F show scanning electron microscope images of the spontaneously-formed hierarchical substructure of the drawn collagen fibers.
Figure 7D:
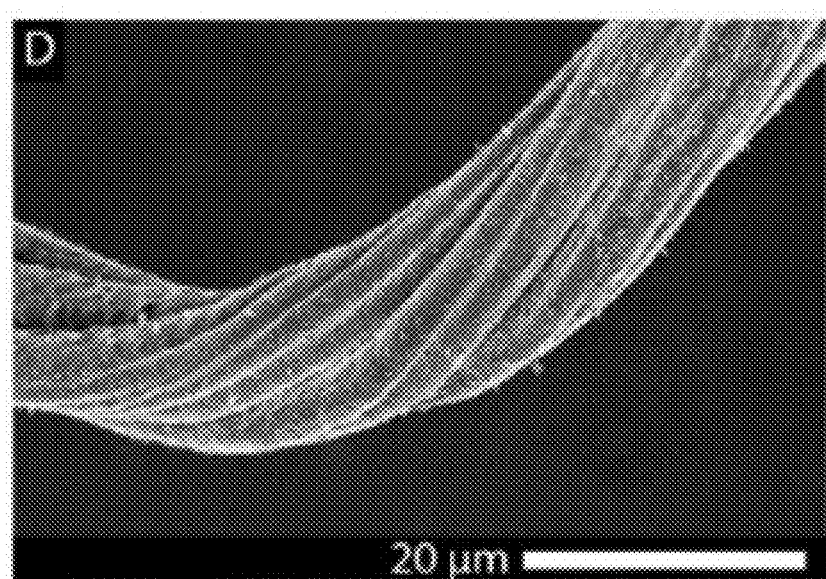
Figure 7E:
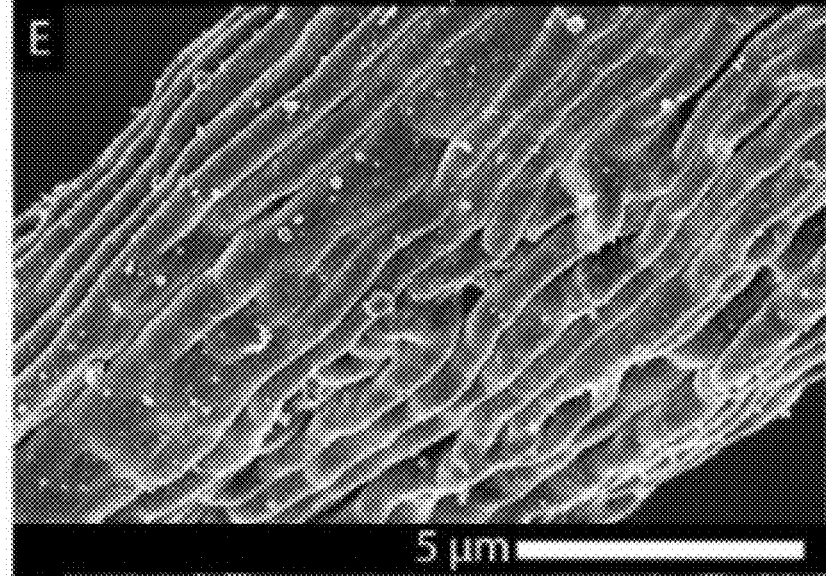
Figure 7F:
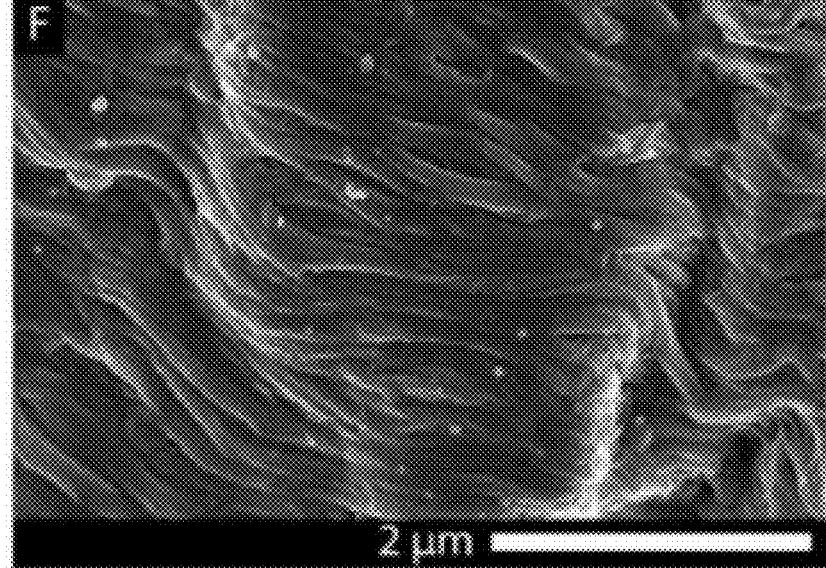

A second set of telo-fibers were prepared for SEM by including 2% decorin in the fiber pulling solution and then incubating the unloaded fibers for 48 hours at 37° C. in phosphate buffered saline containing 1.63% PEG and 2% decorin (FIGS. 7D-7F). After the incubation period, both sets of fibers were then fixed with a recipe of 2.5% glutaraldehyde and 2.5% paraformaldehyde in a 0.1 M sodium cacodylate buffer for 1 hour at room temperature, followed by three washes and a graded series of ethanol exchanges. The fibers were sputter coated with a carbon-platinum coating and SEM imaged (S-4800, Hitachi, Japan) for examination.

Telo-fiber Preparation for Transmission Electron Microscopy

Telo-fibers were drawn with 2% decorin in the solution and prepared for TEM by incubating in an unloaded configuration for 48 hours at 37° C. in phosphate buffered saline with 1.63% PEG and 2% decorin (FIG. 9A-9H). The fixation, sectioning, and imaging protocol used for the TEM of atelo-fibers were repeated for telo-fibers.

Fiber Dissociation

Incubation of the fibers at 37° C., in the absence of strain, resulted in the progressive dissociation of the fibrils. Telo-fibers were evaluated by TEM imaging at two time points: 1 hour and 48 hours. After 1 hour, the most peripheral fibrils began separating from the fiber. After 48 hours, the entire shell had near-completely dissociated and the transitional region had increased empty space between bands of fibrils. The observed changes were in stark contrast to fibers that were held with nominal strain (FIGS. 8A-8F) or in a hypertonic solution (FIGS. 9A-9H) during the incubation period. Strain and osmotic pressure appear to confer intermolecular stability that is required for the persistence of the collagen fibers, in the absence of covalent crosslinks.

Fibril Isolation

Single fibrils from telo-fibers were isolated for TEM imaging by mechanically disrupting the fiber with a glass, micro-tissue grinder (885470-0000, Kimble Chase). A 10 mm central section of the fiber was suspended in the glass vial with 100 µl of phosphate buffer. The glass probe was used to disrupt the fiber until the solution turned opaque and no fiber fragments were visible. 20 µl aliquots were transferred to formvar coated TEM grids (01701-F, Tedpella) for subsequent staining with 1.5% uranyl acetate and imaging. The grids were previously treated with 1% alcian blue to provide a more hydrophilic surface for the fibrils to adhere.

Fibril Periodicity Analysis

The fibril banding periodicity was estimated from the power spectra of TEM images of individual fibrils. Acceptable images were those where at least 500 nm of banded fibril were clearly visible. First, each grayscale image was oriented such that the long axis of one fibril was horizontal and cropped to the largest straight region of banded fibril within the image. Next, the grayscale value of pixels within each column in the cropped image was averaged and the 1-D spatial signal was converted into its frequency domain using discrete Fourier transform. Then, the squared complex modulus of the frequency domain was computed to obtain the power spectral density plot. In this plot, the largest peak falling between 60-80 nm was recognized as the banding periodicity. All image analysis and processing was performed in MATLAB (R2014a, MathWorks).

Results

Figure 4A:
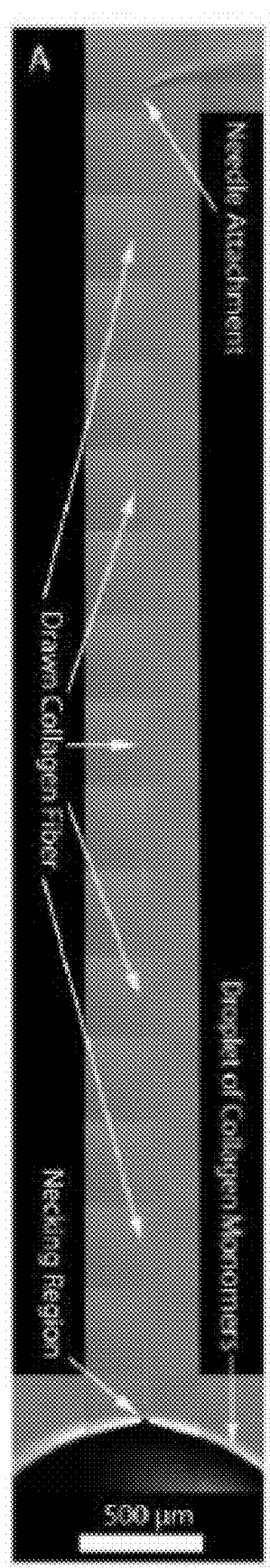
FIGS. 4A-4I show the results of a collagen fiber drawing experiment.
Figure 4B:
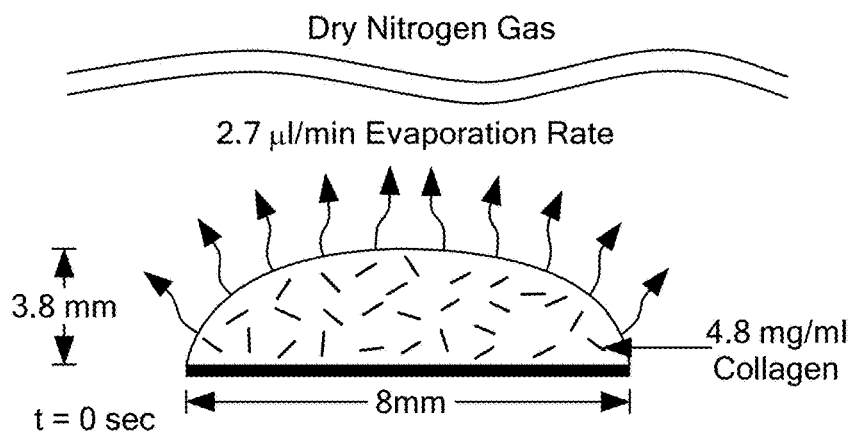
Figure 4C:
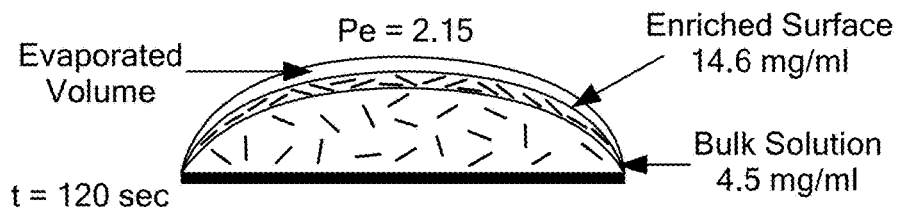
Figure 4D:
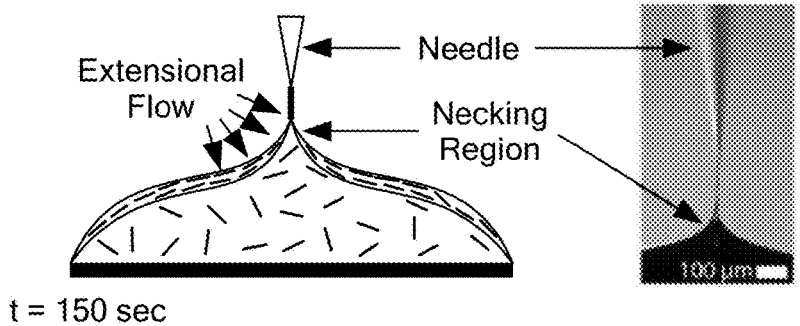
Figure 4E:
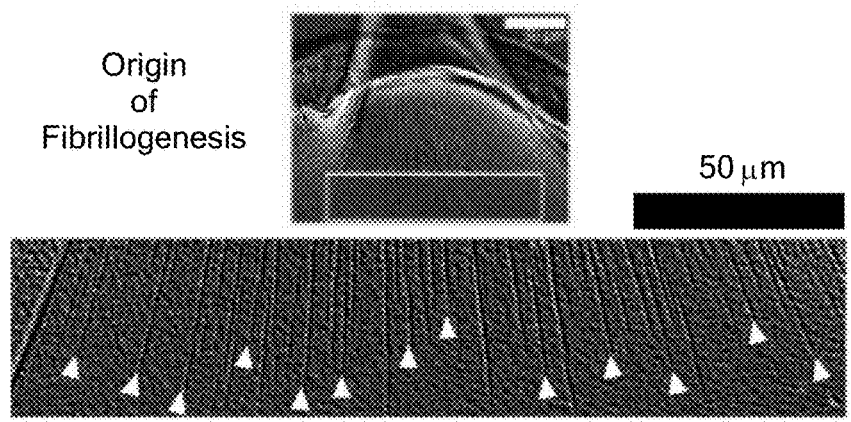

Organized collagen fibers were assembled in the direction of low-level extensional strain rates. Fibers were formed by slowly drawing a micro-needle from the enriched surface of a droplet comprising collagen monomers in solution (FIGS. 4A-4D and 5A-5F). To isolate the location of the fiber initiation, the micro-needle was maneuvered around the droplet surface after drawing a fiber. The attachment point of the fiber to the droplet exhibited a high degree of mobility, suggesting that assembly of the fiber was localized to the small "necking" region where the fiber attaches to the droplet. FIG. 4E confirms that the initiation of the assembly of fibrils within the fiber was indeed confined to the necking region, where newly formed fibrils propagated back into the droplet only a short distance, revealing the precise location of fibril initiation. A thorough microscopic examination of the remaining droplet by DIC microscopy revealed no observable fibrillar structures.

The point of fibril nucleation in the drawn fiber was limited to an area where the geometry and fluid mechanics indicate the presence of an extensional strain field. Extensional strains are known to promote the crystallization of polymers via flow induced crystallization (FIC)[24]. FIC promotes crystallization by two mechanisms: 1) increasing the number of nucleation sites and 2) accelerating crystallization kinetics[25]. FIC is a direct result of the extensional-flow-induced stretching and aligning of polymer chains which is known to lower the entropy of the assembling system and, as a consequence, reduces the change in free energy required for polymer crystallization to occur[26]. Thus, collagen fibril assembly appears to proceed in direct analogy to FIC of polymers.

The extensional strain rate, $\dot{\varepsilon}$, was measured by tracking fluorescent beads during fiber drawing. The maximum observed $\dot{\varepsilon}$ was 0.7 sec$^{-1}$, well below the critical extensional strain rate, $\dot{\varepsilon}_c=1/\lambda$~7000 sec$^{-1}$ (where $\lambda$ is the relaxation time), required to extend a single collagen monomer in an infinitely dilute solution[27]. However, because fibers could not be pulled consistently from the droplet until the droplet was exposed to dry nitrogen for 2.5 minutes, it is certain that the surface collagen concentration on the droplet was far from dilute. A scaling analysis which balanced the surface evaporation speed against collagen diffusion speed suggested that the surface of the droplet increased in concentration to approximately 15 mg/ml during the experimental time course. To determine the surface concentration increase with time and the concentration dependence on depth, optical magnetic micro-viscometry was performed on the droplet during evaporation in dry nitrogen (see SI Text). The data confirmed the existence of a steep concentration gradient from the droplet surface (14.3 mg/ml) to a point 100 μm radially inward where the concentration was 4.6 mg/ml (representative of the bulk droplet concentration). Since the surface concentration is well above the overlap concentration of ~2.5 mg/ml[28], the high level of intermolecular associations is expected to dramatically increase the relaxation time and lower the extensional strain rate necessary to cause molecular alignment by orders of magnitude[29].

Figures 4F, 4G, 4H, 4I:

Repair of fibers was readily demonstrated as well. If a fiber was drawn from the droplet at too high a rate, it fractured at the necking region, and a short fiber segment remained attached to the glass needle (FIG. 4F). The severed fiber could be "repaired" by merely re-introducing it into the droplet and re-drawing at a lower rate (FIGS. 4G-4I). Fiber assembly was reinitiated as the segment end was pulled through the solution, and a visible repair site was formed. Once the junction was created, the fiber continued to be generated without further defect. The data support a route to repair collagen fibers in vivo via exogenous supply of monomer in conjunction with the controlled application of tensile force.

Structural investigation of the drawn fibers with differential interference contrast (DIC) microscopy (FIGS. 6A,6B) showed the high degree of fibrillar alignment and continuity within fibers drawn from either pepsin-extracted collagen monomers that lack telopeptides (atelo-) or acetic acid-extracted collagen monomers with intact telopeptides, (telo-). The slower rate of assembly for atelo-collagen[30] may have permitted the finer organizational control observed in the atelo-fibers. This is possibly due to the increased time for molecular mobility within the growing collagen aggregates to more fully align fibrillar structures with the strain field. Collagen fibers generated from telo-collagen monomers typically possessed fibrils with a slight angular offset from the long axis of the fiber, which could be due to their relatively rapid assembly kinetics "setting" the structure early in the drawing process. Regardless of the collagen source, fibers with remarkable internal fibrillar anisotropy were generated by drawing from a droplet of monomers. As a positive control for pre-assembly of the collagen prior to drawing, fibers were pulled from droplets containing observable, pre-assembled collagen networks (FIG. 6C). The drawing of pre-assembled fibrils preserved the disorganization generated by unguided assembly of the network (FIG. 6D). The images revealed internal fibril entanglement, branching, and most critically, free fibrillar ends which were not observed in the fibers drawn from monomer enriched droplet surface. Because small collagen aggregates that are not detectable with light microscopy could form on the droplet prior to drawing, the droplet surface was examined at high resolution using quick freeze deep etch (QFDE) electron microscopy. Collagen droplets were rapidly frozen using a custom touch freezing technique following 2.5 minutes of exposure to dry nitrogen (the precise time when a fiber could be drawn from the ripened droplet). FIGS. 6E,6F show transmission electron microscopy (TEM) images of the replicated droplet surface. A packed monomeric surface was found on the collagen droplets with little evidence of surface polymerization/aggregation.

The fibers produced by extensional strain were structurally unstable if they were left unloaded in solution for extended periods. This suggests that tensile mechanical forces not only generate the fibers, but they also constitute a stabilizing signal. Incubation of drawn telo-fibers at 37° C. in phosphate buffer for 48 hours led to significant dissociation. The fibril dissociation observed in the unloaded samples was prevented by application of a nominal tension to the fiber during incubation, as confirmed by TEM. The observed strain-stabilization of the collagen fibrillar structure is consistent with strain-induced resistance of collagenous structures to both thermal[22] and enzymatic[23] degradation. It also supports the general concept that tension/strain extends the half-life of assembled biological polymers[31]. Intermolecular stability can be enhanced by reducing the hydration of the collagen fibrils[32,33] and is potentially equivalent to the effect of tensile strain[34]. Thus, the correlation between strain-induced stability and osmotically-induced stability was investigated by incubating drawn fibers in 1.63% polyethylene glycol (PEG), chosen for its physiological match to the oncotic pressure of interstitial fluid[35]. The treatment protected the fibers from dissociation as well as the application of mechanical tension.

FIGS. 7A-7F show the highly-directional orientation and spontaneous development of tendon-like hierarchy induced in fibers by extensional strain. However, in spite of the strong axial organizing effect of the extensional flow, lateral fibrillar associations were often visible between single fibrils in images collected by scanning electron microscopy (FIG. 7C). To more fully reproduce the conditions in vivo and provide a mechanism to control lateral fiber associations (a problem that is observed in native collagen structures when small-leucine rich proteoglycans are absent[36]), fibers were drawn from a solution of collagen containing a physiological concentration of decorin (2%). The addition of the decorin did not affect the ability to draw fibers and an improvement in the discreteness of fibrils was readily observed (FIG. 7F).

Figure 5A:
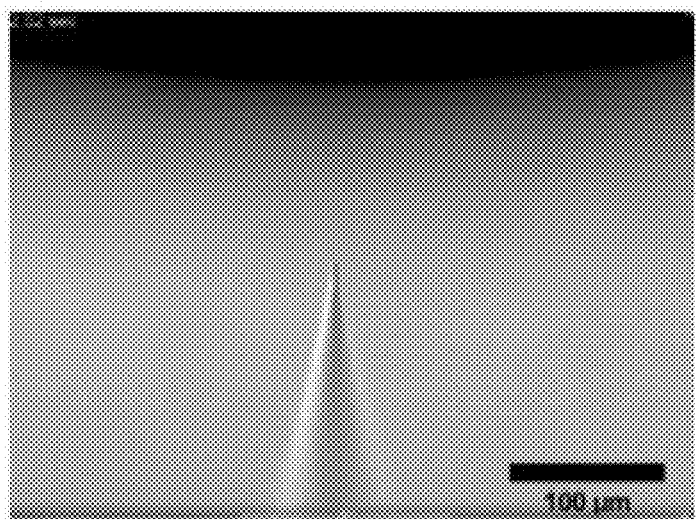
FIGS. 5A-5F show light microscopy (differential interference contrast, DIC) images from a movie of a process of drawing a collagen fiber from a collagen solution under extensional strain. Times of the frames were 2.52 sec, 4.48 sec, 6.44 sec, 7.70 sec, 9.24 sec, and 10.78 sec for FIGS. 5A-5F, respectively.
Figure 5B:
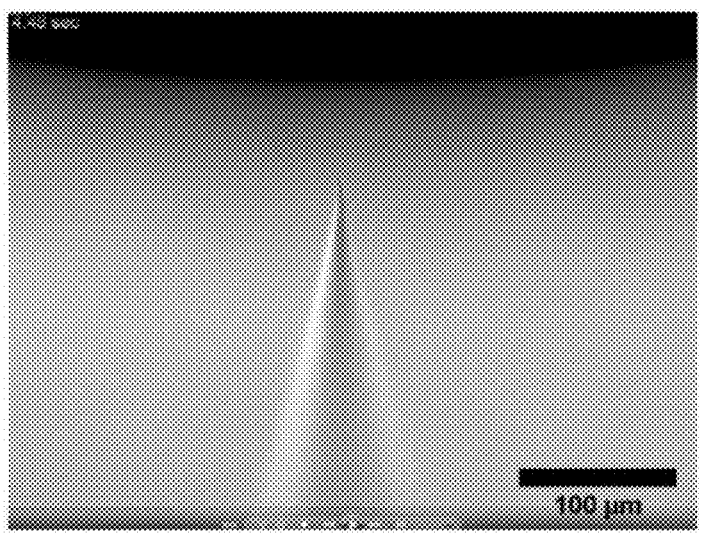
Figure 5C:
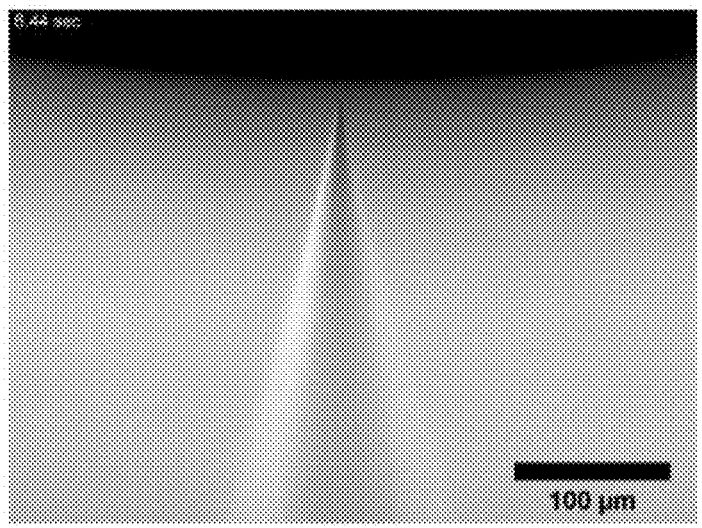
Figure 5D:
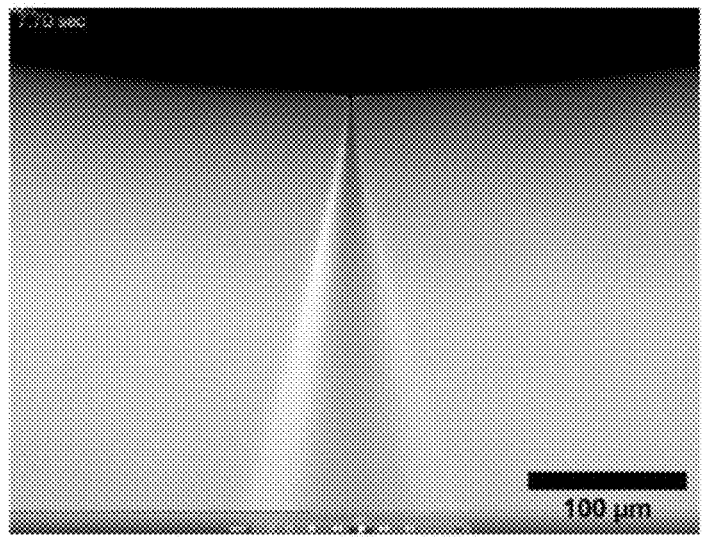
Figure 5E:
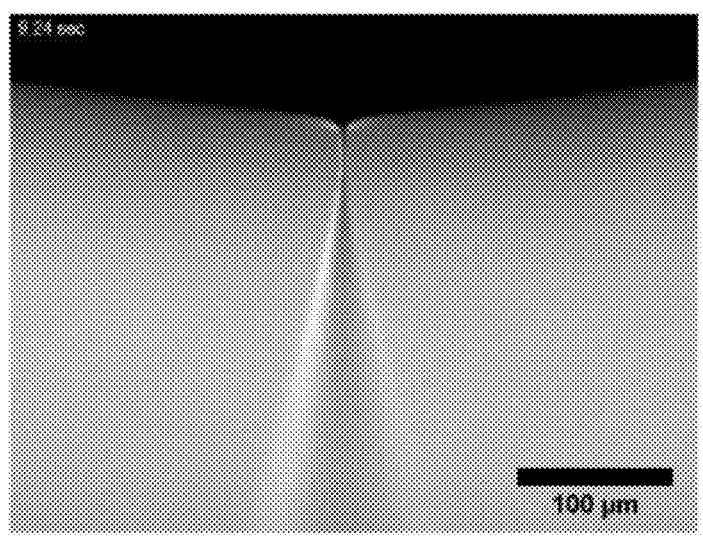
Figure 5F:
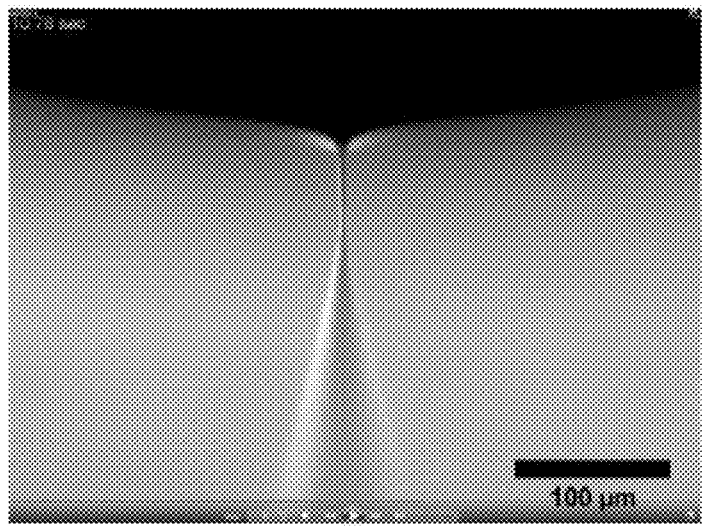
Figures 9D, 9E, 9F:
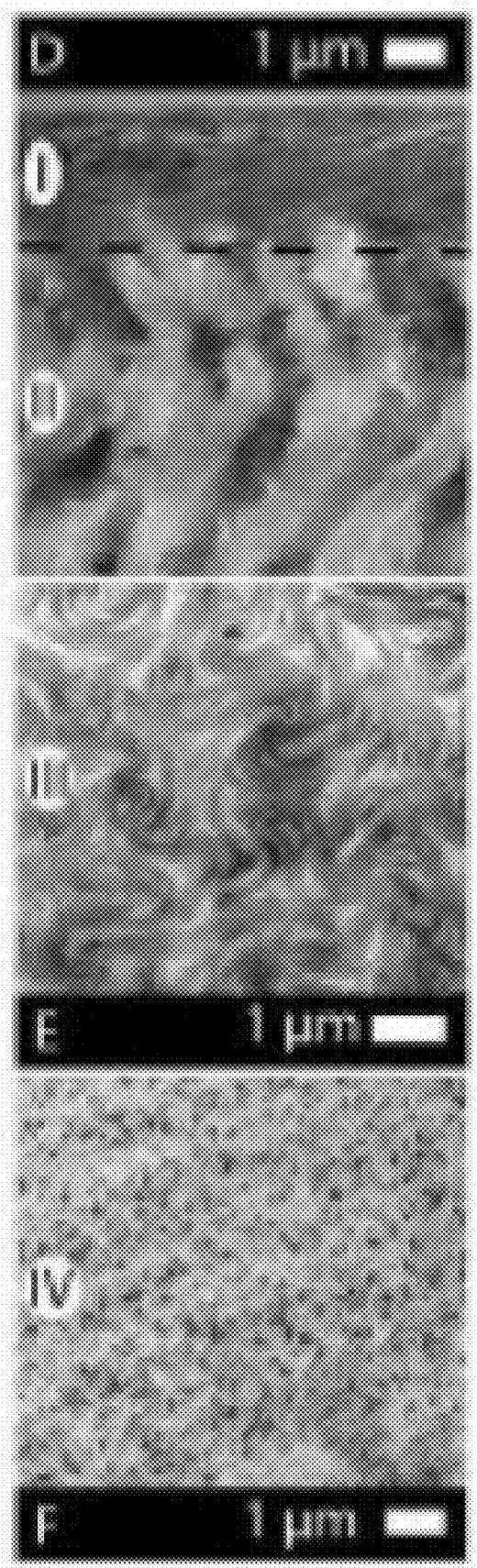
Figure 9G:
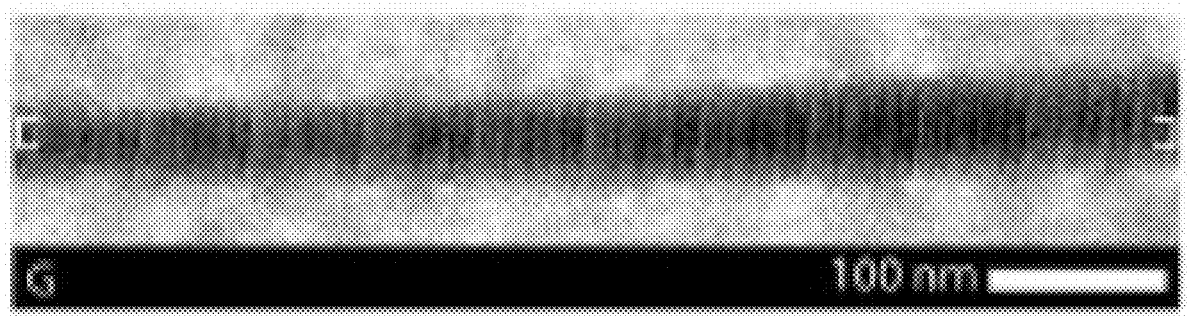
Figure 9H:
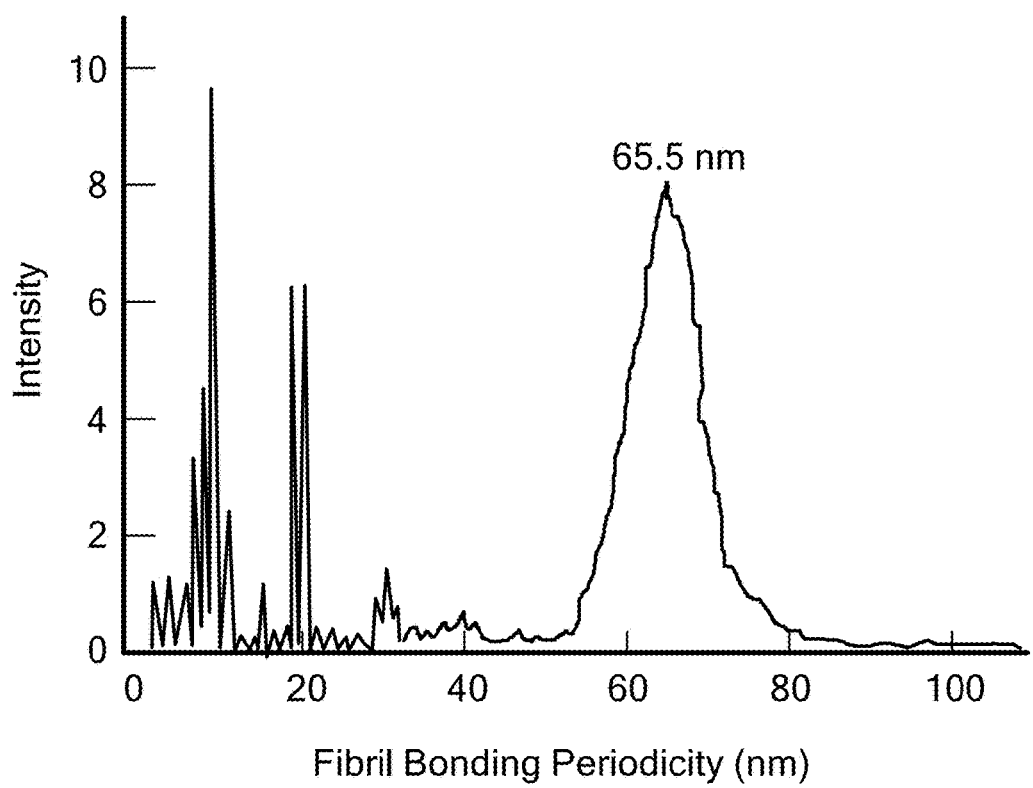
Figure 10:
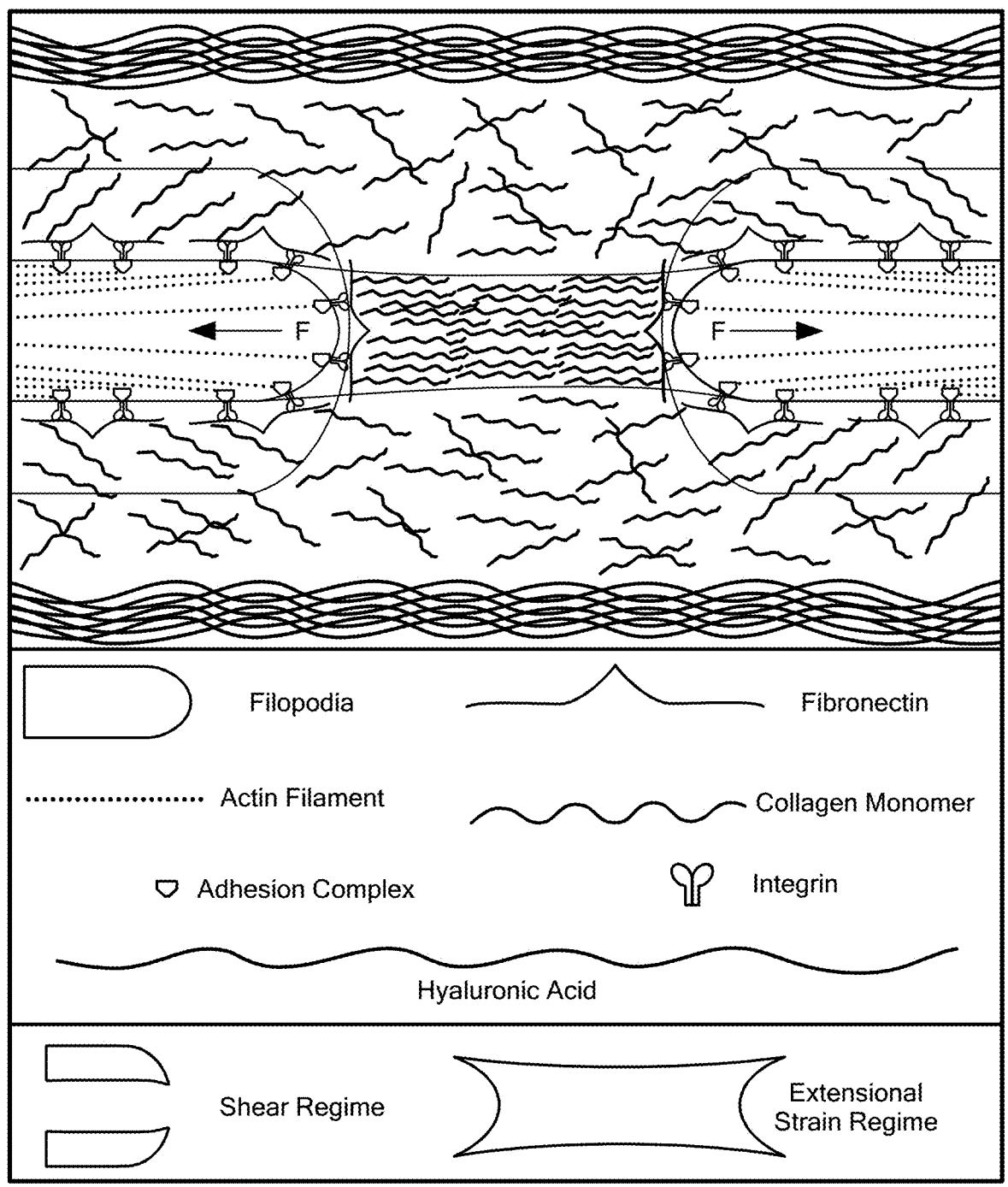
FIG. 10 shows a schematic illustration of how cells are believed to initiate the earliest stage of tissue production in vivo. The schematic displays the filopodia of two cells that are in close proximity to each other. The cells have secreted hyaluronic acid to isolate and raise the concentration of the nearby soluble collagen concentration. When the cells apply a contraction force (e.g. via non-muscle myosin II), F, the two filopodia retract and induce a localized elongational flow. The extensional strain triggers FIC, which both aligns the molecules and results in the continuous formation of fibrils, until the extensional strain falls below a threshold value. Each filopodia retracts until a stalling force resistance is met, or until complete contraction of the actin filament occurs, at which point an invagination may result. The fluid on either side of the filopodia experiences shear-induced strain during the contractions, which serves to pre-align the collagen and form fibrils in conjunction with those formed in the extensional strain regime.

TEM images of fiber longitudinal sections revealed a heterogeneous shell and core structure, with an intermediate transitional zone, for both atelo-fibers (FIGS. 8A-8F) and telo-fibers (FIGS. 9A-9H). The external 5-10 μm thick "shell" comprised continuous, highly-aligned fibrils in both atelo- and telo-fibers. The fibrils were discrete and evenly spaced in the atelo-fibers (FIGS. 8B,8C), while more densely packed in the shell of the telo-fibers (FIG. 9D). Although some regions abruptly switched from shell structure to core (FIG. 8D), the typical atelo-fiber transitional region comprised shorter, wavy fibrils (FIG. 8E). The transitional region between the shell and core for telo-fibers was more extensive, beginning with short bands of fibrils (FIG. 9D), generally at an angle to the long axis of the fiber. The shell to core transition progressively changed to a swirling morphology of short, poorly packed fibrils (FIG. 5E). The core of both the atelo-fibers (FIG. 8F) and telo-fibers (FIG. 9F) had a similar appearance comprising discrete fibrils with isotropic orientation. Fibril banding periodicity for telo-fibers was calculated by isolating a region on an extracted fibril (shown between the brackets in FIG. 9G) and performing a power spectral analysis. The average fibril periodicity for telo-fibers drawn from collagen solution containing the SLRP decorin was 65.4±2.2 nm, depicted in FIG. 9H. The periodicity matches mammalian fibril D-periodic banding.

The transitions in the ultra-structural arrangement of the internal fibrils from the shell of the fiber to the core appeared to reflect the gradient in the concentration of collagen from the surface of the droplet to the bulk (see SI Text). However, the swirling morphology and the angled patterns of fibrils in the transition zone also suggested that there might be variations in the extensional strain rate as a function of the radial position in the necking region (FIGS. 9A-9C). Investigation of the detailed fluid mechanics via fluorescent bead tracking in the necking region during the drawing process revealed that the flow was extensional (ranging from 0.1-0.7 s$^{-1}$) and well-behaved near the surface. However, a clear, central region of recirculation existed at the center, possibly entraining disorganization into the fiber core. Based on the concentration gradient data and the fluid mechanics, it appears that the more concentrated droplet surface experiences FIC as it transits through the necking region, forming highly-aligned fibrillar structures. The lower concentration in the center of the flow field experiences recirculation, resulting in a disorganized fiber core. Thus the ultimate morphology is consistent with the observed fluid mechanics during assembly.

This application claims the priority of U.S. Provisional Application No. 62/092,162 filed 15 Dec. 2014 and entitled "Mechanically Driven, Allosteric Regulation of Extracellular Molecules", and also of U.S. Provisional Application No. 62/232,793 filed 25 Sep. 2014 and entitled "Wearable Microfluidic Tendon Repair Device". Both provisional applications are hereby incorporated by reference in their entireties.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

REFERENCES

1 Wang, H., Abhilash, A., Chen, C. S., Wells, R. G. & Shenoy, V. B. Long-Range Force Transmission in Fibrous Matrices Enabled by Tension-Driven Alignment of Fibers. *Biophys J* 107, 2592-2603 (2014).
2 Bichat, X. *A Treatise on the Membranes in General*. (Cummings & Hilliard, 1813).
3 Mall, F. P. On the development of connective tissues from the connective tissue syncytium. *American Journal of Anatomy* 1, 329-365 (1902).
4 Garrone, R. Collagen, a common thread in extracellular matrix evolution. *Proc Indian Acad Sci (Chem Sci)* 111, 51-56 (1999).
5 King, N. et al. The genome of the choanoflagellate *Monosiga brevicollis* and the origin of metazoans. *Nature* 451, 783-788 (2008).
6 Frosler, J. & Leadbeater, B. S. Role of the cytoskeleton in choanoflagellate lorica assembly. *J Eukaryot Microbiol* 56, 167-173 (2009).
7 Boot-Handford, R. P. & Tuckwell, D. S. Fibrillar collagen: the key to vertebrate evolution? A tale of molecular incest. *Bioessays* 25, 142-151 (2003).
8 Gross, J., Highberger, J. & Schmitt, F. Some factors involved in the fibrogenesis of collagen in vitro. *Proc Soc Exp Biol Med* 80, 4 (1952).
9 Marshall, C. R. Explaining the Cambrian "Explosion" of Animals. *Annu Rev Earth Planet Sci* 34, 30 (2006).
10 Garrone, R., Huc, A. & Junqua, S. Fine structure and physiocochemical studies on the collagen of the marine sponge *Chondrosia reniformis* nardo. *J Ultrastruct Res* 52, 261-275 (1975).
11 Garrone, R. *Phylogenesis of Connective Tissue: Morphological Aspects and Biosynthesis of Sponge Intercellular Matrix*. Vol. 5 252 (S Karger Pub, 1978).
12 Gross, J., Sokal, Z. & Rougvie, M. Structural and chemical studies on the connective tissue of marine sponges. *J Histochem Cytochem* 4, 227-246 (1956).
13 Wolff, J. D. *Das Gesetz der Transformation der Knochen*. (A. Hirschwald, 1892).
14 Gross, J. & Nagai, Y. Specific degradation of the collagen molecule by tadpole collagenolytic enzyme. *Proceedings of the National Academy of Sciences of the United States of America* 54, 1197-1204 (1965).
15 Bhole, A. P. et al. Mechanical strain enhances survivability of collagen micronetworks in the presence of collagenase: implications for load-bearing matrix growth and stability. *Philos Trans A Math Phys Eng Sci* 367, 3339-3362 (2009).
16 Changeux, J. P. 50th anniversary of the word "allosteric". *Protein science: a publication of the Protein Society* 20, 1119-1124 (2011).
17 Motlagh, H. N., Wrabl, J. O., Li, J. & Hilser, V. J. The ensemble nature of allostery. *Nature* 508, 331-339 (2014).
18 Seifert, C. & Grater, F. Protein mechanics: how force regulates molecular function. *Biochimica et biophysica acta* 1830, 4762-4768 (2013).
19 Ejim, O. S., Blunn, G. W. & Brown, R. A. Production of artificial-orientated mats and strands from plasma fibronectin: a morphological study. *Biomaterials* 14, 743-748 (1993).
20 Adhikari, A. S., Mekhdjian, A. H. & Dunn, A. R. Strain tunes proteolytic degradation and diffusive transport in fibrin networks. *Biomacromolecules* 13, 499-506 (2012).
21 Jesudason, R., Black, L., Majumdar, A., Stone, P. & Suki, B. Differential effects of static and cyclic stretching during elastase digestion on the mechanical properties of extracellular matrices. *J Appl Physiol* (1985) 103, 803-811 (2007).
22 Wells, P. B., Thomsen, S., Jones, M. A., Baek, S. & Humphrey, J. D. Histological evidence for the role of mechanical stress in modulating thermal denaturation of collagen. *Biomech Model Mechanobiol* 4, 201-210 (2005).
23 Flynn, B. P. et al. Mechanical strain stabilizes reconstituted collagen fibrils against enzymatic degradation by mammalian collagenase matrix metalloproteinase 8 (MMP-8). *PLoS One* 5, e12337 (2010).
24 Rao, I. & Rajagopal, K. A study of strain-induced crystallization of polymers. *Int J Solids Struct* 38, 1149-1167 (2001).
25 Keller, A. & Kolnaar, H. W. H. *Flow-induced orientation and structure formation*. (Wiley-VCH, 1997).
26 Mackley, M. R. & Keller, A. Flow Induced Polymer-Chain Extension and Its Relation to Fibrous Crystallization. *Phil Trans Roy Soc Lon* 278, 29-& (1975).
27 Nestler, F. H. M., Hvidt, S., Ferry, J. D. & Veis, A. Flexibility of collagen determined from dilute solution viscoelastic measurements. *Biopolymers* 22, 1747-1758 (1983).
28 Gobeaux, F., Belamie, E., Mosser, G., Davidson, P. & Asnacios, S. Power law rheology and strain-induced yielding in acidic solutions of type I-collagen. *Soft Matter* 6, 3769-3777 (2010).

29 Everaers, R. et al. Rheology and microscopic topology of entangled polymeric liquids. *Science* 303, 823-826 (2004).

30 Kuznetsova, N. & Leikin, S. Does the triple helical domain of type I collagen encode molecular recognition and fiber assembly while telopeptides serve as catalytic domains? Effect of proteolytic cleavage on fibrillogenesis and on collagen-collagen interaction in fibers. *The Journal of biological chemistry* 274, 36083-36088 (1999).

31 Dingal, P. D. P. & Discher, D. E. Systems Mechanobiology: Tension-Inhibited Protein Turnover Is Sufficient to Physically Control Gene Circuits. *Biophys J* 107, 2734-2743 (2014).

32 Wenger, M. P., Bozec, L., Horton, M. A. & Mesquida, P. Mechanical properties of collagen fibrils. *Biophys J* 93, 1255-1263 (2007).

33 van der Rijt, J. A., van der Werf, K. O., Bennink, M. L., Dijkstra, P. J. & Feijen, J. Micromechanical testing of individual collagen fibrils. *Macromol Biosci* 6, 697-702 (2006).

34 Masic, A. et al. Osmotic pressure induced tensile forces in tendon collagen. *Nat Commun* 6 (2015).

35 Sverdlik, A. & Lanir, Y. Time-dependent mechanical behavior of sheep digital tendons, including the effects of preconditioning. *J Biomech Eng* 124, 78-84 (2002).

36 Raspanti, M., Viola, M., Sonaggere, M., Tira, M. E. & Tenni, R. Collagen fibril structure is affected by collagen concentration and decorin. *Biomacromolecules* 8, 2087-2091 (2007).

37 Kadler, K. E. The needle in the ECM haystack. *Nat Rev Mol Cell Biol* 15, 769 (2014).

38 Canty, E. G. et al. Actin filaments are required for fibripositor-mediated collagen fibril alignment in tendon. *The Journal of biological chemistry* 281, 38592-38598 (2006).

39 Trelstad, R. L. & Birk, D. E. The fibroblast in morphogenesis and fibrosis: cell topography and surface-related functions. *Ciba Found Symp* 114, 4-19 (1985).

40 Kadler, K. E., Holmes, D. F., Trotter, J. A. & Chapman, J. A. Collagen fibril formation. *The Biochemical journal* 316 (Pt 1), 1-11 (1996).

41 Birk, D. E. & Trelstad, R. L. Extracellular compartments in matrix morphogenesis: collagen fibril, bundle, and lamellar formation by corneal fibroblasts. *The Journal of cell biology* 99, 2024-2033 (1984).

42 Birk, D. E. & Trelstad, R. L. Fibroblasts create compartments in the extracellular space where collagen polymerizes into fibrils and fibrils associate into bundles. *Annals of the New York Academy of Sciences* 460, 258-266 (1985).

43 Canty, E. G. et al. Coalignment of plasma membrane channels and protrusions (fibripositors) specifies the parallelism of tendon. *The Journal of cell biology* 165, 553-563 (2004).

44 Birk, D. E., Silver, F. H. & Trelstad, R. L. in *Cell Biology of the Extracellular Matrix* (ed E. D. Hay) (1991).

45 Birk, D. E., Nurminskaya, M. V. & Zycband, E. I. Collagen fibrillogenesis in situ: fibril segments undergo post-depositional modifications resulting in linear and lateral growth during matrix development. *Dev Dyn* 202, 229-243 (1995).

46 Wolff, J. in [translated from the 1892 original, *Das Gesetz der Transformation der Knochen* by P. Maquet and R. Furlongi] (Springer Verlag, Berlin, 1986).

47 Thompson, D. W. *On growth and form*. (Cambridge University Press, 1917).

48 Kieny, M. & Chevallier, A. Autonomy of tendon development in the embryonic chick wing. *J Embryol Exp Morphol* 49, 153-165 (1979).

49 Neath, P., Roche, S. M. & Bee, J. A. Intraocular pressure-dependent and -independent phases of growth of the embryonic chick eye and cornea. *Invest Ophthalmol Vis Sci* 32, 2483-2491 (1991).

50 Coulombre, A. J. The role of intraocular pressure in the development of the chick eye. II. Control of corneal size. *AMA Arch Ophthalmol* 57, 250-253 (1957).

51 Kalson, N. S. et al. Nonmuscle myosin II powered transport of newly formed collagen fibrils at the plasma membrane. *Proceedings of the National Academy of Sciences of the United States of America* 110, E47434752 (2013).

52 Kapacee, Z. et al. Tension is required for fibripositor formation. *Matrix biology: journal of the International Society for Matrix Biology* 27, 371-375 (2008).

53 Kadler, K. E., Hill, A. & Canty-Laird, E. G. Collagen fibrillogenesis: fibronectin, integrins, and minor collagens as organizers and nucleators. *Curr Opin Cell Biol* 20, 495-501 (2008).

54 Young, R. D. et al. Three-dimensional aspects of matrix assembly by cells in the developing cornea. *Proceedings of the National Academy of Sciences of the United States of America* 111, 687-692 (2014).

55 Toole, B. P. & Trelstad, R. L. Hyaluronate production and removal during corneal development in the chick. *Developmental biology* 26, 28-35 (1971).

56 Scott, J. E. & Hughes, E. W. Proteoglycan-collagen relationships in developing chick and bovine tendons. Influence of the physiological environment. *Connect Tissue Res* 14, 267-278 (1986).

57 Laurent, T. C. & Ogston, A. G. The Interaction between Polysaccharides and Other Macromolecules. 4. The Osmotic Pressure of Mixtures of Serum Albumin and Hyaluronic Acid. *The Biochemical journal* 89, 249-253 (1963).

58 Scott, J. E., Cummings, C., Brass, A. & Chen, Y. Secondary and tertiary structures of hyaluronan in aqueous solution, investigated by rotary shadowing-electron microscopy and computer simulation. Hyaluronan is a very efficient network-forming polymer. *The Biochemical journal* 274 (Pt 3), 699-705 (1991).

59 Legant, W. R., Chen, C. S. & Vogel, V. Force-induced fibronectin assembly and matrix remodeling in a 3D microtissue model of tissue morphogenesis. *Integr Biol (Camb)* 4, 1164-1174 (2012).

60 Harris, A. K., Stopak, D. & Wild, P. Fibroblast traction as a mechanism for collagen morphogenesis. *Nature* 290, 249-251 (1981).

61 Meshel, A. S., Wei, Q., Adelstein, R. S. & Sheetz, M. P. Basic mechanism of three-dimensional collagen fibre transport by fibroblasts. *Nature cell biology* 7, 157-164 (2005).

62 Kress, H. et al. Filopodia act as phagocytic tentacles and pull with discrete steps and a load-dependent dependent velocity. *Proceedings of the National Academy of Sciences of the United States of America* 104, 1163311638 (2007).

63 Ahamadi, F., Bosorgmehr, R. & Razeghi, E. Relationship between serum leptin level and laboratory and anthropometric indices of malnutrition in patients on hemodialysis. *Indian journal of nephrology* 18, 105111 (2008).

64 Birk, D. E., Zycband, E. I., Winkelmann, D. A. & Trelstad, R. L. Collagen fibrillogenesis in situ: fibril segments are intermediates in matrix assembly. *Proceed-* ings of the National Academy of Sciences of the United States of America 86, 4549-4553 (1989).
65 Kadler, K. E., Holmes, D. F., Graham, H. & Starborg, T. Tip-mediated fusion involving unipolar collagen fibrils accounts for rapid fibril elongation, the occurrence of fibrillar branched networks in skin and the paucity of collagen fibril ends in vertebrates. *Matrix biology: journal of the International Society for Matrix Biology* 19, 359-365 (2000).
66 Birk, D. E., Zycband, E. I., Woodruff, S., Winkelmann, D. A. & Trelstad, R. L. Collagen fibrillogenesis in situ: fibril segments become long fibrils as the developing tendon matures. *Dev Dyn* 208, 291-298 (1997).
67 Saeidi, N. et al. Disorganized collagen scaffold interferes with fibroblast mediated deposition of organized extracellular matrix in vitro. *Biotechnol Bioeng* 109, 2683-2698 (2012).
68 Saeidi, N., Sander, E. A. & Ruberti, J. W. Dynamic shear-influenced collagen self-assembly. *Biomaterials* 30, 6581-6592 (2009).
69 Saeidi, N. et al. Molecular crowding of collagen: a pathway to produce highly-organized collagenous structures. *Biomaterials* 33, 7366-7374 (2012).
70 Ritzakis, N. *Method and evaluation for minimization of mechanical effects from impact velocity for the optimization of freezing quality of metal mirror impact freezers* Master's Degree thesis, Northeastern University, (2011).
71 Fletcher, G. C. Dynamic light scattering from collagen solutions. I. Translational diffusion coefficient and aggregation effects. *Biopolymers* 15, 2201-2217 (1976).
72 Claire, K. & Pecora, R. Translational and Rotational Dynamics of Collagen in Dilute Solution. *J Phys Chem B* 101 (1997).
73 Bueno, E. M. & Ruberti, J. W. Optimizing Collagen Transport through Track-Etched Nanopores. *J Memb Sci* 321, 250-263 (2008)

The invention claimed is:

1. A method of promoting collagenous tissue remodeling in a subject in need thereof, the method comprising the steps of:
   (a) administering to a tissue remodeling site in the subject a tissue remodeling solution comprising collagen monomers and initially devoid of pre-existing collagen fibrils; and
   (b) inducing strain or strain rate in the tissue remodeling solution at the tissue remodeling site, whereby collagen incorporation of the collagen monomers, collagen fibril assembly, collagen fibril fusion, and/or collagen fibril disassembly is stimulated at the tissue remodeling site.

2. The method of claim 1, further comprising the step of:
   (a0) prior to step (a), implanting an internal sheath into the subject, the sheath surrounding the tissue remodeling site.

3. The method of claim 1, further comprising the steps of:
   (c) monitoring one or more parameters in a sample of extracellular fluid obtained from the tissue remodeling site; and
   (d) adjusting the administration or composition of the remodeling solution based on said one or more parameters.

4. A device for promoting tissue remodeling in a subject in need thereof, the device comprising:
   (i) a dispensing module, comprising:
      a reservoir for a tissue remodeling solution;
      an infusion pump for transporting the tissue remodeling solution from the reservoir and returning an extracellular fluid from the subject;
   (ii) a delivery catheter for transporting the tissue remodeling solution from the infusion pump to a tissue remodeling site in the body of the subject; and
   (iii) a programmable control module for controlling the pump and/or the composition of the tissue remodeling solution, wherein the control module is programmed to control tissue remodeling by regulating delivery and/or composition of the tissue remodeling solution to the tissue remodeling site, so as to promote collagen fibril assembly, fusion, disassembly, and/or realignment at the tissue remodeling site; and
   wherein the dispensing module further comprises a mixing system for mixing the returned extracellular fluid with the tissue remodeling solution and/or with one or more additional reagents for transport to the tissue remodeling site through the delivery catheter.

5. The device of claim 4, wherein the dispensing module further comprises:
   one or more additional reservoirs for one or more additional reagent solutions, and wherein
   the mixing system is configured for mixing the one or more additional reagent solutions with the tissue remodeling solution and/or the returned extracellular fluid prior to its transport to the tissue remodeling site.

6. The device of claim 5, wherein the mixing system comprises a microfluidic chip.

7. The device of claim 5, wherein the programmable control module controls the mixing of said one or more reagent solutions with the tissue remodeling solution and/or the returned extracellular fluid.

8. The device of claim 5, wherein the programmable control module controls the pH, ionic strength, and/or temperature of the tissue remodeling solution and/or the one or more reagent solutions.

9. The device of claim 4, further comprising:
   (iv) a return catheter for transporting extracellular fluid from the tissue remodeling site back to the device for analysis.

10. The device of claim 9, wherein the return catheter comprises a filter to exclude cells and assembled fibers.

11. The device of claim 9, further comprising:
    (v) a sensor for detecting a concentration of one or more components of extracellular matrix fluid at the tissue remodeling site, the sensor providing an output related to the one or more components to the control module.

12. The device of claim 11, wherein the sensor is a microcalorimeter.

13. The device of claim 11, wherein the sensor detects the concentration of collagen.

14. The device of claim 13, wherein the sensor detects the concentration of two or more different species of collagen.

15. The device of claim 11, comprising two or more sensors detecting the concentrations of two or more different components of the extracellular matrix fluid.

16. The device of claim 11, wherein the mixing system further comprises a mixing chamber, a microfluidic chip, or a combination thereof.

17. The device of claim 16, further comprising a microdialysis module for conditioning of returned extracellular fluid before it is transported back to the tissue remodeling site.

18. The device of claim 4, further comprising:
    a temperature control mechanism for controlling the temperature of the tissue remodeling solution stored in the dispensing module or in another module connected with the dispensing module.

19. The device of claim 18 that provides both cooling for long-term storage of reagents and warming to body temperature of solutions prior to administration to the subject.

20. The device of claim 4 configured as a wearable device.

21. The device of claim 4 further comprising one or more valves.

22. The device of claim 4, wherein the control module is remote from dispensing module.

23. The device of claim 22, wherein the control module is a cell phone, computer, or other wireless device that transmits and receives signals to and from the dispensing module.

24. The device of claim 4 further comprising said tissue remodeling solution, and/or one or more additional solutions, in one or more reservoirs of the dispensing module.

25. The device of claim 4 further comprising one or more additional catheters for administration of the tissue remodeling solution at different locations at or near the tissue remodeling site.

26. The device of claim 4, wherein the delivery catheter comprises a needle for administration of the solution by injection at or near the tissue remodeling site.

27. The device of claim 4, wherein bidirectional flow of tissue remodeling fluid is provided, to and from the dispensing module.

28. The device of claim 27, wherein bidirectional flow is provided by reversible flow through the delivery catheter.

29. The device of claim 27, wherein bidirectional flow is provided by the combined action of the delivery catheter and a return catheter.

30. The device of claim 27, wherein extracellular fluid collected from the tissue remodeling site is collected in a fluid chamber for analysis.

31. The device of claim 4, further comprising a muscle stimulation module that provides electrical stimulation of one or more muscles of the subject in the area surrounding the tissue remodeling site.

32. The device of claim 4, further comprising a passive motion device that provides extensional strain in the area surrounding the tissue remodeling site.

33. An in vitro method of producing one or more collagen fibrils, the method comprising the steps of:
   (a) providing a collagen solution comprising collagen monomers and initially devoid of collagen fibrils; and
   (b) inducing strain in the solution, whereby collagen monomers from the solution assemble into one or more collagen fibrils.

34. A method to aid in preventing injury or tissue damage in a subject in need thereof, the method comprising the steps of:
   (a) administering to a tissue remodeling site in the subject a tissue remodeling solution comprising collagen monomers and initially devoid of pre-existing collagen fibrils, wherein the tissue remodeling site is suspected of being subject to future injury or tissue damage; and
   (b) inducing strain or an extensional strain rate in the tissue remodeling solution at the tissue remodeling site, whereby collagen incorporation of the collagen monomers, collagen fibril assembly, collagen fibril fusion, and/or collagen fibril disassembly is stimulated at the tissue remodeling site.

* * * * *